US012603158B2

(12) United States Patent
Paschke et al.

(10) Patent No.: US 12,603,158 B2
(45) Date of Patent: Apr. 14, 2026

(54) DATA PROCESSING DEVICE AND METHOD FOR THE EVALUATION OF MASS SPECTROMETRY DATA

(71) Applicant: Thermo Fisher Scientific (Bremen) GmbH, Bremen (DE)

(72) Inventors: Carmen Paschke, Bremen (DE); Hans Grensemann, Hude (DE); Torsten Ueckert, Lilienthal (DE); Kai Fritzemeier, Stuhr (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 539 days.

(21) Appl. No.: 17/743,367

(22) Filed: May 12, 2022

(65) Prior Publication Data

US 2022/0392582 A1 Dec. 8, 2022

Related U.S. Application Data

(63) Continuation of application No. 15/318,101, filed as application No. PCT/EP2015/062913 on Jun. 10, 2015, now abandoned.

(Continued)

(30) Foreign Application Priority Data

Aug. 28, 2014 (GB) .................................... 1415273.0
Nov. 5, 2014 (GB) .................................... 1419699.2

(51) Int. Cl.
*G01N 33/48* (2006.01)
*G01N 30/72* (2006.01)
(Continued)

(52) U.S. Cl.
CPC ......... *G16C 20/20* (2019.02); *G01N 30/7266* (2013.01); *G01N 30/88* (2013.01);
(Continued)

(58) Field of Classification Search
None
See application file for complete search history.

(56) References Cited

U.S. PATENT DOCUMENTS

2002/0194646 A1 12/2002 Pogue et al.
2004/0088762 A1 5/2004 Oriedo et al.
(Continued)

FOREIGN PATENT DOCUMENTS

CN 102017058 A 4/2011
CN 103270575 A 8/2013
(Continued)

OTHER PUBLICATIONS

O'Neil, Elizabeth J. "Object/relational mapping 2008: hibernate and the entity data model (edm)." Proceedings of the 2008 ACM SIGMOD international conference on Management of data. 2008.*

(Continued)

*Primary Examiner* — Anna Skibinsky

(57) ABSTRACT

A data processing device comprises a processor unit adapted to process a plurality of initial data vectors provided by a chromatograph and/or a mass spectrometer, the processing being carried out in one, two or more processing steps producing items of processed data, and a storage unit adapted to save and retrieve initial data vectors and/or items of processed data, in particular processed data vectors or identified compounds, and/or items of additional data, in particular properties of the sample introduced in the mass spectrometer. Each item of processed data and/or additional data is connected to at least one initial data vector, and wherein the processor unit is adapted to group, select and/or modify initial data vectors and/or items of processed data according to one or more items of additional data.

20 Claims, 6 Drawing Sheets

Related U.S. Application Data

(60) Provisional application No. 62/012,228, filed on Jun. 13, 2014.

(51) Int. Cl.

| | |
|---|---|
| *G01N 30/88* | (2006.01) |
| *G16C 20/20* | (2019.01) |
| *H01J 49/16* | (2006.01) |
| *H01J 49/42* | (2006.01) |

(52) U.S. Cl.
CPC .... *G01N 2030/8831* (2013.01); *H01J 49/164* (2013.01); *H01J 49/425* (2013.01)

(56) References Cited

U.S. PATENT DOCUMENTS

| | | |
|---|---|---|
| 2005/0063864 A1 | 3/2005 | Sano et al. |
| 2006/0123349 A1 | 6/2006 | Wakabayashi |
| 2008/0281847 A1 | 11/2008 | Berntenis et al. |
| 2009/0148960 A1* | 6/2009 | Oda ...................... G01N 30/84 |
| | | 422/68.1 |
| 2011/0315868 A1 | 12/2011 | Hirabayashi et al. |
| 2012/0004854 A1 | 1/2012 | Fernandez et al. |
| 2013/0297230 A1 | 11/2013 | Kawase |
| 2014/0097338 A1 | 4/2014 | Eiler |
| 2015/0018242 A1 | 1/2015 | Lyng et al. |
| 2016/0139151 A1 | 5/2016 | Ward et al. |

FOREIGN PATENT DOCUMENTS

| | | |
|---|---|---|
| EP | 2450815 A1 | 5/2012 |
| JP | 2008096183 A | 4/2008 |
| WO | WO-2004038602 A1 | 5/2004 |
| WO | WO-2005060608 A2 | 7/2005 |
| WO | WO-2005113812 A2 | 12/2005 |
| WO | WO-2013149963 A1 | 10/2013 |

OTHER PUBLICATIONS

Peng, "The Research and Development of Mass Spectrometry Measurement and Control Software Based on Object-oriented Technique", A Dissertation Submitted for the Degree of Master, South China University of Technology, Guangzhou, China, 2010, pp. 1-66.

Sharma et al., "A Mass Spectrometry Proteomics Data Management Platform", Molecular & Cellular Proteomics, 2012, vol. 11 (9), pp. 824-831.

Yin, Kangping, The Analysis of MS Data Based on Bayesian Method, China Academic Journal Electronic Publishing House, Master's Dissertation, East China Normal University, School of life Science, Bioinformatics, 2012, pp. 1-118.

\* cited by examiner

DATA PROCESSING DEVICE AND METHOD FOR THE EVALUATION OF MASS SPECTROMETRY DATA

CROSS-REFERENCE TO RELATED APPLICATION

This application is a continuation under 35 U.S.C. § 120 and claims the priority benefit of co-pending U.S. patent application Ser. No. 15/318,101 filed Dec. 12, 2016, which is a National Stage application under 35 U.S.C. § 371 of PCT Application No. PCT/EP2015/062913 filed Jun. 10, 2015, which claims the priority benefit of U.S. Provisional Patent Application Ser. No. 62/012,228 filed Jun. 13, 2014, and in addition claims the priority benefit of United Kingdom applications GB1415273.0 filed Aug. 28, 2014, and GB1419699.2 filed Nov. 5, 2014. The disclosures of each of the foregoing applications are incorporated herein by reference.

FIELD

The invention relates to a data processing device adapted to the processing of mass spectrometry data, a mass spectrometry setup and a method for the evaluation of mass spectrometry data. Aspects of the invention also relate to post acquisition data analysis software for evaluation of multiple datasets, particularly in the fields of proteomics (protein ID, quantification, detection of posttranslational modifications), metabolomics, metabolism studies, compound identification, development and detection of disease, pharmaceutical and toxicological markers, quantification of all of the above. Certain aspects of this invention relate also to control of instruments based on such post acquisition data analysis. Such feedback could be performed during a measurement (e.g. an LC/MS acquisition) or after it.

BACKGROUND

The application of mass spectrometry to biology allows for a detailed analysis of processes at a cellular level, as discussed in the article by Patterson and Aebersold, nature genetics suppl. 33, 311 (2003). Two major fields of biological mass spectrometry are metabolite analysis and protein/peptide analysis. Both may be used to assess the state of a biological system, e.g. regarding the reaction on an external stimulus or a state of health or disease. Similar tasks exist in food safety and toxicology.

Many biological mass spectrometry studies start from a general study where a set of N samples is present. These are then formed or subject to an experiment, which may comprise a gas or liquid chromatography-mass spectrometry (GC/MS or LC/MS) or liquid chromatography-tandem mass spectrometry (LC/MS/MS) or ion mobility-tandem mass spectrometry (IMS/MS) measurement of each sample or of subsets of the samples in the study, or indeed any combination of chromatography separation, mobility separation, mass analysis and possibly additional spectrographic measurements.

For the measurement, different samples may be modified to be individually recognizable, e.g. by chemical attachment of a mass tag, which may comprise isotopic, metallic or other labels, or by modification with an isotopic label. Depending on the measurement strategy and target organism, the label may be chemically attached before or after a proteolytic treatment, administered as food or in a growth medium or otherwise connected with the analyte.

With such labelling a plurality of sub-samples may be mixed to form a combined sample, which is then subjected to a mass spectrometry measurement. The sub-samples may then be identified within the combined sample by the mass of the mass tag, isotopic patterns generated from the mass differences between the differently labelled sub-samples and/or mass differences that are revealed when performing an MS/MS ($MS^2$) or $MS^n$ experiment. Depending on the label or tag the mass differences may be small fractions of an atomic mass unit (labels containing different isotopes (typically of C, N, O, H) in different positions such that the unit-mass stays the same), one or several mass units (conventional isotope labels as used e.g. with iTRAQ, TMT, SILAC) or many mass units (metals).

Various properties of the samples, also named factors, are known that reflect the variability of the experiment. However, it is in general not a priori known which of the various factors do influence the measurements. Actually finding the factors or "study variables" that have an influence on the measurements is one underlying goal of the experiment. Frequently there exist different "questions" to be assigned to an experiment regarding how different study variables result in different (or not different) measurement results. An example of such a study may be found in WO 2013/149963 A1.

A primary challenge in research of this nature relates to how the various study variables are connected with the measurements in order to give qualitative and quantitative information on the state of the biological system. As mass spectrometry data frequently results in extremely large data sizes (e.g. 0.2 to 5 GB of data for the LC/MS of one sample) the processing takes substantial time even on modern (as of 2014) computer workstations.

Biological mass spectrometry data evaluation in general suffers from a fragmentation of data evaluation tools. In recent years many different tools have been developed by different scientific and commercial groups for evaluation of biological mass spectrometry data. While some complete workflows exist for targeted analysis (for example as disclosed by U.S. Pat. No. 7,269,517, which is rooted in fluorescence assays), support for exploratory research and for conversion to targeted methods is still weak. This is partly because acquisition related data evaluation and laboratory information management aspects are typically realized in separate software packages. Additionally, typical software packages rely on quite rigid process and data models that make it difficult to adapt the systems to new tasks.

Against this background it is a goal of this invention to provide a fast and flexible data evaluation system for biological mass spectrometry data.

SUMMARY

According to an aspect of the present invention there is provided a data processing device, comprising a processor unit adapted to process a plurality of initial data vectors provided by a chromatograph and/or a mass spectrometer, the processing being carried out in one, two or more processing steps producing items of processed data, and a storage unit adapted to save and retrieve initial data vectors and/or items of processed data, in particular processed data vectors or identified compounds, and/or items of additional data, in particular properties of the sample introduced in the chromatograph and/or mass spectrometer, wherein each item of processed data and/or item of additional data is connected to at least one initial data vector, and wherein the processor unit is adapted to group, select and/or modify initial data vectors and/or items of processed data according to one or more items of additional data.

The data processing device can be realized as a single computer or in a distributed form with a number of processing devices interconnected by a wireless and/or wired and/or fiber-based network. Further, the processor unit may contain a plurality of processor cores in one or several interconnected units.

Initial data vectors give the result of a measurement conducted over a period of time, wherein preferably a measured intensity is given depending on a second parameter, e.g. elution time or mass-to-charge ratio (m/z), in particular a mass spectrum. These data can be produced by a chromatograph or, preferably, by a mass spectrometer coupled to a liquid chromatography-electrospray ion source or a MALDI ion source. In particular, an initial data vector can be a data vector with value pairs of measured intensity versus mass (or mass over charge). However, especially for a mass analyzer of the Orbitrap type, the initial data vector may be alternatively given as a spectrum over a defined frequency range or a transient given over a defined time span. Herein the term 'mass' and like terms (e.g. 'mass spectrum') are to be understood to refer not just to mass but also any quantities in mass spectrometry that are directly related to mass, for example frequency in Fourier transform mass spectrometry and time in time-of-flight mass spectrometry.

An initial data vector may be an unprocessed data vector or may have undergone some initial processing, e.g. a conversion into a mass scale and/or a calibration of a mass or time scale. The initial processing may also contain a filtering of the raw spectra, so that only a selected number of measured peaks are treated as initial data vectors.

The processing steps preferably comprise adjusting a mass or time scale and/or normalizing the intensity of data vectors, so that the items of processed data are data vectors and/or identifying a primary compound, in particular a peptide, based on one or more data vectors and/or identifying a parent compound, in particular a protein, based on a number of identified primary compounds, so that the item of processed data may be a string such as a name or a representation of a sequence or the structure formula of a compound. The identification may comprise a query to an additional database, which e.g. relates measured fragments with digested proteins and/or peptides. Further, one or more of the processing steps could comprise a validation of identified compounds. For targeted or metabolomic analysis the identification may comprise comparison with a list of masses and/or elemental compositions derived from an initial set of compounds by application of rules, e.g. to simulate metabolic transformations in organisms.

When two or more consecutive processing steps are carried out, it is not necessary for every intermediate processing step to produce items of processed data. This allows for processing steps that export or modify existing data to be carried out as intermediate processing steps.

Additional data are preferably information concerning the conditions of a particular measurement, such as date and/or time and/or instrument used. For proteomics or metabolomics experiments, the additional data preferably contains one or more factors or study variables such as the time elapsed after administering a drug or other information concerning the preparation of a sample. Additional data also comprise further information such as the database(s) searched for identification of the peptide or protein or if and in which database a spectral match was found. Additional data preferably depend at least partly on information that cannot be directly inferred from an initial data vector. Thus, the items of additional data may comprise study variables or influence factors such as the tissue or organism the sample was taken from, the administered drug, the dosage of the drug, the time after administration of the drug, the age or sex of the patient, the sample preparation. Items of additional data may further comprise a time and/or date of measurement, an identifier of the mass spectrometer used or any other parameter related to the measurement of a specific sample, e.g. including data introduced for quality control measures.

In particular, initial data vectors may be grouped based on additional data, e.g. all spectra measured from a particular tissue may be added up or averaged, one or more items of processed data may be selected based on additional data, the mass scale of initial data vectors or processed data vectors may be modified based on additional data. Preferably, initial data vectors may alternatively or additionally be grouped based on items of processed data, such as an identified peptide or protein.

The storage unit preferably comprises memory devices which save information in the form of electrical charges, such as a random access memory, or memory devices which save information in the form of magnetic domains, such as a hard drive.

A data processing device according to the invention has various advantages in view of the prior art:

The flexibility of use with customer or third-party "plugins", since plugins generally have to store "unexpected" additional data in a way that integrates well and doesn't disturb processes that may later fall under cGMP regulations.

The initial data vectors are kept unchanged and can be accessed at any time during the processing of the data. Influence factors or further information are connected to the input vectors in a way that facilitates retrieving and or modifying items of processed data corresponding to an initial data vector.

Because initial data vectors, resulting items of processed data and items of additional data are connected, i.e. logically linked, a set of corresponding data items can be retrieved based on e.g. a given item of additional data. By grouping or selecting initial data vectors and/or items of processed data according to an item of additional data, potential influence factors can be determined without a priori knowledge.

When e.g. the time and/or date the sample was taken or the sample preparation is given as an item of additional data, the calibration and/or normalization of a mass spectrum may be adapted according to observed variations in the instruments response, so that the accuracy of the measured data can be improved.

Processing of the data may also include visualization of the data. The flexible retrieving of items of processed data based on a given item of additional data allows for flexible "experimental designs" in order to assess the influence of different study variables. The visualization may comprise user-configurable tables, scatter plots, histograms, bar charts, pie charts and/or Venn diagrams.

Preferably, each initial data vector is assigned a unique identifier, and each item of processed data is connected to an item of processed data from a preceding processing step of the same initial data vector and/or directly to the initial data vector.

In general, an item of processed data created in a particular processing step is connected to the item of processed data created in the processing step directly preceding this particular processing step. For some initial data vectors or resulting intermediate processed data, a subsequent processing step may not result in an item of processed data, or in an "empty" item of processed data. This can occur e.g. for database searches in order to identify a compound, in particular a peptide or protein. In this case, a search in one or more additional database/s may be performed especially for those initial data vectors which gave no result in the search of the first database.

Preferably, the storage unit is adapted to store the initial data vectors, the items of processed data and/or the items of additional data in a relational database.

The relational database may comprise one, two or more files in the file system of the storage unit, in particular a set of associated files.

Preferably, the relational database comprises a fixed number of predefined tables and a number of dynamic tables, wherein at least one of the predefined tables contains a definition of dynamic data types, and wherein one dynamic table is created for each dynamic data type.

The predefined tables preferably contain administrative information of the database and in particular manage additional data; the administrative information may comprise a date of creation of the database file(s), the version of the database engine used for creation of the database. Advantageously, the predefined tables comprise a list of dynamic tables and/or a list of the columns of dynamic tables and/or a definition of dynamic data types. Further, the administrative information may comprise a semantic or ontological description of dynamic data types, indicating e.g. that a column of a dynamic table contains a retention time or a spectrum of a measured sample.

Preferably, the storage unit comprises a data interface for defining dynamic data types and/or modifying the relational database, so that dynamic tables can be added and/or columns can be added to existing dynamic tables.

The dynamic data types are based on and may comprise a number of properties of a predefined data type, such as integer or floating-point number, string or byte array. Advantageously, the user can define new dynamic data types to store additional data, in particular information concerning the experiment such as an administered drug and/or the period of presence of the drug in the metabolism, and the definition of a new dynamic data type results in the creation of a new dynamic table in the database. If the initial data vectors are provided by a mass spectrometer coupled to a chromatograph, at least one of the dynamic data types may comprise a retention time. In general, the definition of dynamic data types is not performed by an end user, but by a programmer enhancing the existing database with added functionality.

Preferably, the definition of dynamic data types may comprise references to converters, wherein a storage form of a property of the defined dynamic data type is converted into a processing form when retrieving data from the storage unit, and the processing form of an item of the defined dynamic data type is converted into the storage form when saving data to the storage unit. This allows for storing complex or structured properties, so that arbitrary data can be saved.

When defining a dynamic data type, converters may be added, e.g. in the form of a third-party module. For example, initial data vectors may be represented by XML files containing a list of value pairs. An additional converter may be added to compress the XML file and store it in a field of a dynamic table as a byte array. When retrieving the initial data vector, the byte array is converted back into an XML file. In this way, 'simple' properties such a retention time or charge may be stored in the same table as the corresponding spectrum. Details of the reference may depend on the operating system of the data processing device, so that e.g. if a converter is contained in a program library, the reference may comprise the address and/or function name and/or parameter definition of the converter.

It is a preferred feature of the present invention that the storage unit is adapted to store connections between items of a first and items of a second dynamic data type, and that the relational database comprises one further dynamic table containing the connections between the items of the first and the items of the second dynamic data type.

Additionally, connections between the first and a third and/or the second and a third dynamic data type may be defined. When these additional connections are defined, at least one further dynamic table is created for each further pair of dynamic data types that can be connected. Advantageously, an unlimited number of connections may be defined.

Preferably, one dynamic table is created for each connection between two dynamic data types, and the dynamic table of a connection contains one or more columns for storing items of additional data and/or items of processed data.

Storing additional data in the dynamic table of connections allows for annotating the connection of two specific items with information specifically connected to both items. For example, in a sample containing peptides, a connection may be defined between a peptide and a modification, wherein the position of a particular modification in the peptide is stored in the dynamic table of the connection.

Advantageously, the data interface of the storage unit allows for adding new data fields as well as new connections to the relational database, so that additional columns and/or dynamic tables are created and can be accessed.

According to a preferred embodiment of the invention, at least one of the dynamic data types is adapted for the characterization of the sample and/or the targeted compound.

According to a particularly preferred embodiment of the invention, the samples introduced in the mass spectrometer contain proteins and/or peptides, in particular digested proteins, wherein the dynamic data types comprise protein, in particular comprising a sequence and a description and a weight, and peptide, in particular comprising a sequence and a charge, wherein the processing comprises a processing step of identifying peptides and a subsequent processing step of identifying proteins, and wherein the relational database comprises a table of identified proteins and a table of identified peptides.

Preferably, connections between peptides and proteins are also defined; as explained, above, a position of the peptide in the protein may also be stored in the corresponding dynamic table. Additionally, modification may be defined as a further dynamic data type, in particular comprising a name and a mass difference, wherein the relational database comprises an additional table for modifications and an additional for the position of modifications in an identified peptide. Further, similar tables could be defined for an identified compound, a functional group, the position of the functional group in the compound, and for a possible modification of the functional group, e.g. a deuteration. The processing step of identifying a peptide or protein may be carried out with help of one or more searches in one or more external databases.

According to a particularly preferred embodiment of the invention, the samples introduced in the mass spectrometer contain a drug and/or a metabolite, wherein the user-defined data types comprise drug, in particular comprising name, period of effect and tissue of the sample, metabolite, in particular comprising chemical formula and/or name, and modification, in particular comprising charge, mass and position wherein the processing preferably comprises a processing step of identifying metabolites.

The data processing device can be seen in certain embodiments to be a system for identifying compounds of a sample (e.g. such as proteins, metabolites and other compounds as mentioned herein). The data processing device can be seen in certain embodiments to be a system for quantifying compounds of a sample Preferably, the data processing device of the invention further comprises a module interface, which allows for adding dynamic modules that implement processing steps, wherein the dynamic modules can save and/or retrieve items of data as well as add dynamic data types and/or modify tables of the relational database.

Advantageously, the relational database stores information about modules such as input data, output data and optional or required parameters.

According to a preferred embodiment of the invention, the data processing device comprises a workflow interface for defining sequences of processing steps, wherein processing steps can be performed by default modules and/or dynamic modules, wherein the workflow interface provides services to modules which allows them to retrieve data from the relational database, define dynamic data types, and to save data in the relational database.

Advantageously, processing steps can be performed both by default modules initially provided with the data processing device and by dynamic modules, which can be programmed by the user or provided by a third party.

According to a preferred embodiment of the invention, the workflow interface is adapted to define a first and a second workflow, each workflow comprising a sequence of one or more processing steps, wherein the first workflow is carried out before the second workflow, wherein the processed data or output data of the first workflow is used as input data for the second workflow.

Advantageously, this allows for the definition of a two-stage analysis process. Based on the intermediate result produced by the first workflow, a number of different second workflows may be carried out. Preferably, at least the output data of the first workflow are stored in a result file. This is particularly advantageous when some parts of the processing are always the same, independent of the study variables (items of additional data) selected for processing, so that these common parts are executed only once. Intermediate results produced by the common processing steps can be stored and loaded for further processing according to the variable aspects. This has the advantage that computationally expensive aspects of the data processing need not be repeated (e.g. Sequest-search, Percolator, general validation steps). The separation of common and variable processing steps eases sharing of data and saves storage space, because intermediate results are stored only once.

According to a particularly preferred embodiment of the invention, the workflow interface is adapted to define a number of first workflows, each workflow comprising a sequence of one or more processing steps, wherein the first workflows are carried out independently by the processor unit, and wherein the second workflow comprises a processing step of combining, comparing and/or analyzing the processed data resulting from the number of first workflows.

Advantageously, an arbitrary number of workflows may be defined.

According to a particularly preferred embodiment of the invention, the data processing device is adapted to store a workflow comprising a sequence of processing steps in a workflow file, wherein the workflow file preferably comprises a list of initial vectors to be processed, and wherein the data processing device is further adapted to store at least the items of processed data, preferably initial data vectors, items of processed data and items of additional data, from a workflow being carried out by the processor unit in a result file, in particular a relational database file.

Preferably, a workflow produces or modifies a result file, in particular a file containing the whole relational database. By means of stored workflows, analyzing different sets of measurements with the same processing steps can simply be performed by changing the list of initial data vectors to be processed.

According to an especially preferred embodiment of the invention, before carrying out a subsequently defined workflow, the processor unit is adapted to compare the processing steps and the list of initial data vectors of the subsequently defined workflow to the processing steps and the list of initial data vectors of one or more stored workflows, and if both the processing steps and the list of initial data files of a stored workflow correspond to the initial processing steps of the subsequent workflow, data from the corresponding result file of that stored workflow is retrieved in place of carrying out the initial processing steps of the subsequently defined workflow.

Advantageously, carrying out all of the time-consuming processing steps can be avoided when processed data from a suitable previous workflow are available; this is particularly useful for time-consuming processing steps which often occur in proteomics due to the size of the measured data files.

Preferably, the storage unit is further adapted to store for each item of processed data which default or dynamic module created or modified this item of processed data. This facilitates automatic reprocessing of the data and allows for verification of the data and/or error recognizing and tracing back errors.

The data processing device preferably comprises visualization means, in particular a computer monitor and/or a printer, wherein the processor unit is further adapted to visualize the grouped, selected and/or modified data of one or more processing steps using the visualization means.

Preferably, the data processing device further comprises interaction means, in particular a keyboard and/or a mouse, wherein the interaction means and the visualization means are adapted to operate the workflow interface, i.e. send commands to and/or receive information from the workflow interface.

Advantageously, the user can view and edit workflows with a graphical user interface.

The data processing device preferably comprises an instrument interface for sending commands to and receiving data from a mass spectrometer.

Preferably, the processor unit is adapted to process a first set of initial data vectors, performing one or more processing steps, wherein the instrument interface is adapted to send commands to the mass spectrometer, initiating the measurement of a second set of initial data vectors, and to receive the second set of initial data vectors from the mass spectrometer, wherein the storage unit is adapted to save the second set of initial data vectors, and wherein the processor unit is adapted to process the second set of initial data vectors, performing one or more processing steps.

Preferably, the processor unit is further adapted to change the commands for measuring the second set of data depending on the result of the processing of the first set of initial data vectors. This has the advantage of allowing for data-dependent acquisition, such as measuring specific m/z-ranges or performing ion selections and/or fragmentations when a predefined peak pattern was found or a database search gave inconclusive results.

According to another aspect of the present invention, there is provided a mass spectrometry setup comprising a data processing device with an instrument interface and a mass spectrometer connected to the instrument interface, comprising in particular a mass analyzer of the Orbitrap type coupled to a liquid chromatography—electrospray ion source.

According to yet another aspect of the present invention, there is provided a method for identifying and/or quantifying peptides and/or proteins and/or metabolites, comprising the steps of a. Acquiring initial data vectors of a plurality of samples by a mass spectrometry setup, in particular a mass spectrometry setup according to the invention, b. Assigning one or more items of additional data to each initial data vector, c. Grouping or selecting a number of initial data vectors according to an item of additional data, in particular selecting only those initial data vectors for which the item of additional data has a predefined value, d. Processing the grouped or selected number of initial data vectors in one or more processing steps comprising preferably modifying a mass scale and/or an intensity of the initial data vectors, e. Performing a search in a database of known mass spectra from peptides and/or proteins and/or metabolites, and f. Outputting the names and/or properties of the peptides and/or proteins and/or metabolites identified by the database search.

Advantageously, the user does not have to select manually which initial data vectors, i.e. mass spectra, need to be processed e.g. for the identification of proteins present in a particular tissue. Information concerning the tissue of a measured sample is preferably stored as an item of additional data in the storage unit of a data processing device, in particular a relational database. In particular when many different tissues are analyzed, this simplifies and accelerates the processing of the data.

Optionally the step of acquiring initial data vectors may further comprise performing liquid chromatography or (differential) ion mobility separation or any other physical separation and acquiring initial data vectors as a function of the separation parameter enzymatically, physically or chemically treating the sample before mass analysis or separation to ease analysis and/or to establish a parameter that allows to identify data from different samples via mass spectrometry performing data dependent MS, MS/MS or MS″ analysis based on signal intensities, isotope ratios, isotopic patterns, predefined mass differences, masses obtained from a list or based on mass differences or masses determined from a full or partial execution of this method, either based on a previous experiment or results obtained earlier in time from the same experiment while it is still ongoing.

According to a preferred embodiment of the present invention, the method further comprises at least one of the steps of g. Assigning one or more items of additional data to each item of processed data, h. Grouping or selecting a number of processed data items according to an item of additional data directly assigned to the processed data item or assigned to an item of processed data from a preceding processing step of the same initial data vector and/or directly to the initial data vector, i. Processing the grouped or selected number of processed data items in one or more steps preferably comprising a validation of the processed data items, wherein one or more of the steps may be repeated before the final step of outputting the names and/or properties of the peptides and/or proteins and/or metabolites.

In accordance with a further aspect of the invention, a method of mass spectrometry is provided comprising steps of providing a plurality of samples; optionally pooling these samples as sub-samples to form combined samples; acquiring mass spectrometry data of the samples with an MS or LC/MS system; associating study variables with samples or sub-samples and the related mass spectrometry data; providing a user interface for selection of a first desired visualization of the relationship of study variables and measurement results; processing the mass spectrometry data to allow such visualization; interactively visualizing the results as a first table or graph to show a relationship between study variables and mass spectrometry data; providing a user interface for changing the desired visualization to give a second desired visualization; identifying processing steps that are common for generation of the first and second desired visualization; only performing processing steps that are not common to generate the second desired visualization, and; interactively visualizing the results as a second table or graph to show a relationship between study variables and mass spectrometry data.

In accordance with a still further aspect of the invention, a method of mass spectrometry is provided comprising steps of providing a plurality of samples; optionally pooling these samples as sub-samples to form combined samples; generating measurement results from the samples with an MS or LC/MS system, optionally further comprising ion mobility or differential ion mobility analysers; associating study variables with samples or sub-samples and the related measurement results; providing a user interface for defining a first processing method or workflow; computing and optionally storing intermediate results from the measurement results based on said first processing method; providing a user interface for defining a second processing method or workflow, this second processing method or workflow to be performed after the first processing method, and; providing a user interface for visualization of the processing method, thus visualizing relationships between study variables and measurement results; wherein the second processing method and visualization may be changed by the user and the second processing method may be executed without a need to re-compute the results of the first processing method.

It is efficient to allow assignment and evaluation of different study variables and grouping of samples under different criteria after the measurement, such that potential factors of influence can be determined without a priori knowledge.

A major improvement against the prior art is that instead of relying on predefined experimental designs, the "questions" on the experiment may be formulated "ad hoc" by the user. The other major improvement is efficient use of computational resources by splitting the processing workflow in a constant and a variable part, such that common results (e.g. database searches in proteomics) need not be re-computed. Thus influence factors like e.g. tissue/organism, drug, dosage, time after administration, illness, age, sex, patient/individual, operator, and sample preparation, may be completely assessed. While the system does not set any restrictions (like predefined "experiment designs"), it is still possible to save processing methods and to re-apply them to different sets of samples.

Optionally the steps of providing samples and of performing mass spectrometry may further comprise: performing liquid chromatography or (differential) ion mobility separation or any other physical separation and observing mass spectrometry data as a function of the separation parameter; enzymatically, physically or chemically treating the sample before mass analysis or separation to ease analysis; enzymatically, physically or chemically treating the sample before mass analysis or separation to establish a parameter that allows to identify data from different sample via mass spectrometry, and/or; performing data dependent MS, MS/MS or $MS^n$ analysis based on signal intensities, isotope ratios, isotopic patterns, predefined mass differences, masses obtained from a list or based on mass differences or masses determined from a full or partial execution of this method, either based on a previous experiment or results obtained earlier in time from the same experiment while it is still ongoing.

The software that implements the foregoing methods preferably does not create a data-matrix of "scans", but instead the original data are left "untouched", but the user attaches the experimental factors to the input data vectors and the sample management, processing and visualization tools carry the experimental factors as "annotations" to the data, which can be grouping by vectors (e.g. organism, dosage, time after administration), averaging various replicates, etc.)

The different experimental designs preferably are not in the/a database, but "in the head of the user". Thus, on the basis of an "intermediate result" the user can apply different experimental designs ("evaluations in view of different "vectors") "on the fly", but when a design is selected and stored it can be only one experimental design per file which may then be applied to other data.

The visualization may comprise tables, user-configurable tables and or scatter plots, histograms, bar charts, pie charts and Venn diagrams.

Note the connection with the "two stage" analysis process that makes this approach computational cost efficient.

Some parts of the processing may be always the same, independent of the experimental variables selected for grouping/evaluation. These parts advantageously may be executed only once. These intermediate results can be stored and loaded for further processing according to the variable aspects. The system allows reprocessing of a report that just re-groups the study variables (=experimental variables, factors).

Computationally expensive aspects of the data processing need not be repeated (e.g. Sequest-search, Percolator, general validation steps) need not be repeated. The separation of common and variable steps eases sharing of data and saves storage space, because intermediate results are stored only once.

The processing steps may be split between different groups, for example one or more invariant first processing methods may be executed by the lab/experiment/measurement team, while the second processing method is performed by a specialized team.

In accordance with another aspect of the invention, a method of mass spectrometry is provided comprising steps of providing a plurality of samples; performing a mass spectrometric analysis of the samples; providing a programming interface for user specified programs; providing a data storage interface for data generated by the user specified processing modules; providing a user interface for assigning study variables to samples and/or mass spectrometric analyses; providing a user interface for defining a processing workflow comprising predefined processing modules and user specified processing modules; performing the user specified processing, and; visualizing processing results, the visualization comprising data generated by predefined processing modules and data generated by user specified processing modules. User specified processing modules are programs that may be written by any third party and interact with the data and processing methods of the core program via the programming and data interface.

Mass spectrometric analysis may be one of MS, LC/MS, IMS/MS, DIMS/MS, LC/(D) IMS/MS wherein the "MS" collectively denotes mass spectrometry and MS/MS or $MS^n$ methods.

In accordance with yet another aspect of the invention, a method of identifying metabolites by mass spectrometry is provided comprising steps of accepting a plurality of samples containing metabolites of one or more substances; performing a mass spectrometric analysis of the samples, thus generating mass spectrometry data; providing a programming interface for user specified programs; providing a data storage interface for data generated by the user specified processing modules; providing a user interface for assigning study variables to samples and/or mass spectrometric analyses; providing a user interface for defining a processing workflow comprising predefined processing; modules and user specified processing modules; performing the user specified processing, and; visualizing processing results, the visualization comprising data generated by predefined processing modules and data generated by user specified processing modules.

The method may further comprise steps of accepting substance information from the user or an external data source, and/or; generating candidate metabolite information from said substances by rules or retrieval of metabolite information from an external data source.

The user-specified processing may further comprise identifying candidate metabolites in the mass spectrometry data by the candidate metabolite information; visualizing the relationship between study variables and candidate metabolites; visualizing the relationship between data generated by user specified processing modules and candidate processing modules, data generated by user specified processing modules and candidate metabolites.

In some preferred embodiments of the invention, the processing results are stored in a database. In typical database storage interfaces, tables can be saved as known during development, e.g., peptides, peaklists, metabolites, and relations may be established between the tables. The data storage interface aspect of the invention (the "entity data service") now allows the user to save not only the "known" data types, but "whatever you want" (e.g. sample management information, patient address, arbitrary information from customer supplied nodes, . . . )

extend existing data (i.e. e.g. add a new column to an existing table)

not only extend data, but also "connections" (=relations)

store arbitrary data types and define properties for these data types, e.g. how they may be plotted by a visualization module (e.g. "category", "x-y", integer, . . . ).

Moreover, the flexibility of the entity data service is a "door opener" for use with universal customer or third-party "plugins", because all "general" plugins will have to store "unexpected" data in a way that integrates well and doens't disturb processes that may later fall under cGMP regulations.

This means for the applications that, e.g. for a protein, the position of a peptide in the protein and the (flanking) amino acids next to the protein can be stored as a connection; connections can be annotated, e.g. modifications: peptide: the modification can be present several times and another entry has the position; and a user can write a filter to provide sequence.

One exemplary view is a simple array of color coded markers for the presence or non-presence of an analytical feature in a sample, or conversely for an analytical feature the study variables or samples for which this is true. The analytical feature may, for example, be presence of a certain protein or metabolite or the presence of a compound that is specific to a certain metabolic pathway or organism.

Some further advantages which may be achieved by embodiments of the invention include:

flexibility in processing, allowing change of processing steps late in the experimentation and data analysis process; ad hoc definition of relationships between samples and grouping of samples; and minimization of data to be handled for data grouping and evaluation in relation to variables: N (number of MS experiments) raw data files, and N database (Sequest, Moscot, *Andromeda*) searches and false detection rate evaluations are aggregated to a single intermediate result. In proteomics this may be a set of identified peptides together with the associated user defined study variables. This data set may then be used for further grouping, processing, visualization, etc.

Advantageously, in embodiments, the system has the capability of storing "unforeseen" (in the sense of not expected during development of the software product) data (additional data) and making this data available for further steps (processing and visualization) in exactly the same way as data and data types expected during development of the software product.

DETAILED DESCRIPTION OF EMBODIMENTS

In order to further understand the invention, embodiments will now be described in detail by way of example with reference to the accompanying drawings, which are for illustration only and are not intended to and do not limit the scope of the invention.

LIST OF FIGURES

Figure 1:
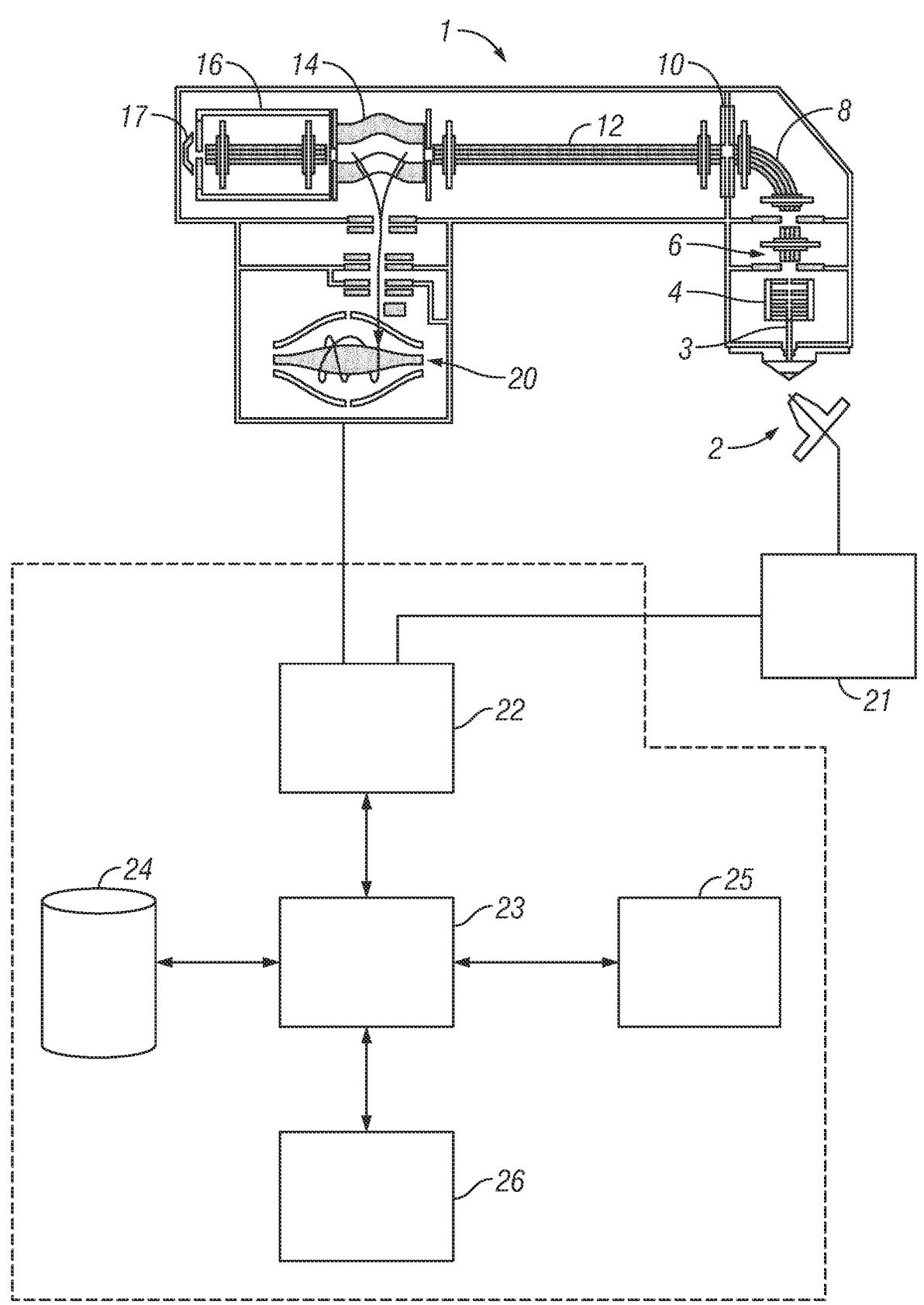
FIG. 1 shows a schematic view of a mass spectrometer coupled to a data processing device in a preferred embodiment of a mass spectrometry setup.

Referring to FIG. 1, a preferred embodiment of a mass spectrometry setup is shown, comprising a mass spectrometer 1 utilizing an electrostatic trap 20 in the form of an Orbitrap mass analyzer and a data processing device 30. The instrument further comprises an electrospray ion source 2 operated at atmospheric pressure. It will be appreciated that other ion sources could be used, such as matrix-assisted laser desorption/ionisation (MALDI) or any other inlet ionization. Preferably, sample is injected into the electrospray ion source via a liquid chromatography setup 21. Another preferred method is gas chromatography (GC) followed by electron or chemical or photoionization.

Ions from the electrospray ion source 2 pass through a transfer capillary 3 to a stacked ring ion guide (S-lens) 4 and then through an injection flatapole 6 and a bent flatapole 8. Neutral clusters and droplets may fly unimpeded through gaps between the rods of the bent flatapole and thus do not contribute to the measured signal. The pressure in the region of the S-lens to the bent flatapole is typically 1-10 mbar, so that a degree of collisional cooling occurs in the bent flatapole. An ion gate 10 in the form of a fast split lens controls the entry of the ions into an RF-only transport multipole 12, which in the shown embodiment is an octapole and typically held at a pressure less than 104 mbar. In a preferred alternative embodiment, the transport multipole 12 is at least partially implemented as a quadrupole mass filter, thus allowing for a very fast mass selection, and may further comprise one or two additional lenses and/or an additional flatapole.

From the transport multipole the ions enter a C-trap 14 typically with a pressure therein of $(0.1\text{-}4.0)\times10^{-3}$ mbar (for example $5\times10^{-4}$ mbar). Optionally the ions may be passed for further cooling into a gas-filled dead-end Higher energy Collisional Dissociation (HCD) cell 16 comprising RF multipole rods typically with a pressure of $(1\text{-}20)\times10^{-3}$ mbar (e.g. $5\times10^{-3}$ mbar). From there the ions are passed back into the C-trap. The HCD cell is provided with an axial field for this purpose, e.g. by providing a retarding voltage on the back of the HCD. The HCD cell is separated from the C-trap by a single diaphragm, which allows easy tuning of the HCD cell. If required, the RF and axial field applied to the HCD cell can be set to provide for fragmentation of ions therein. The HCD cell allows better trapping while maintaining a certain pressure in the C-trap and thus in the Orbitrap, because the HCD cell is i) longer and ii) at a higher pressure than the C-trap. Ions are injected from the C-trap into the Orbitrap mass analyser 20. The HCD might be a pseudo MS3 device, where a first non mass-selective fragmentation has been performed in the ion source region and one of the fragments selected in the RF multipole. Besides HCD, for example low energy collision induced dissociation, electron capture or electron transfer dissociation or photodissociation could be used.

The vacuum in the Orbitrap compartment is preferably below $7 \times 10^{-10}$ mbar, although a pressure of up to $2 \times 10^{-9}$ mbar could be used. The m/z of larger, slower ions may be determined at such pressures in the Orbitrap, which may be due to the total travelled path that decreases with mass faster than the mean free path increases with mass. The number of ions in the Orbitrap is preferably controlled automatically (automatic gain control) by measuring the total ion charge using a short pre-scan before the analytical scan and from that calculating the ion injection time for the analytical scan. For high scan rates, the previous analytical scan can be used as the pre-scan to optimize the scan cycle time. Additionally or alternatively, an ion collector 17 may be placed behind the HCD collision cell and used for independent charge detection, which periodically (e.g. every 5-10 sec) checks and adjusts the accuracy of the automatic gain control. Transients detected by image current detection in the Orbitrap mass analyzer are processed in a data processing device using Fourier Transformation to convert the transient signals into frequency components and then m/z.

While the mass spectrometry setup described above contains a mass analyzer of the Orbitrap type, it will be appreciated that other mass analyzers may also be used, based e.g. on a time-of-flight measurement or a physical separation of the different masses in a sector field or mass-dependent losses such as in a quadrupole instrument. Further, the exact setup or combination of mass filter, collision cell and mass analyzer may be varied; for some electrostatic trap instruments, sequential application of suitable voltages may replace different stages of mass spectrometry that are physically separate in other instruments.

The data processing device 30 comprises an instrument interface 22, which is adapted to send commands to or operate the mass spectrometer 1 and liquid chromatography setup 21 and to receive measured data or status information from the instrument, a processor unit 23 and a storage unit 24. Preferably, the data processing device further comprises visualization means 25, in particular a display and/or a printer, and interaction means 26, in particular a keyboard and/or a mouse, so that the user can view and enter information.

The instrument interface 22 can be any interface known from the state of the art that is adapted to send data to and receive data from the mass spectrometer 1 and/or the ion source comprising the liquid chromatography setup 21. The mass spectrometer may comprise a control unit (not shown) adapted to communicate with the instrument interface 22, to set voltages on one or more of the ion-optical elements of the mass spectrometer and/or receive signals from detectors or sensors in the mass spectrometer. The control unit may contain a processor unit adapted to perform a pre-processing of the measured signals such as a Fourier transformation, data compression, peak identification, peak picking, mass calculation, peak annotation (e.g. with exact mass, area, elemental composition, accuracy information for intensity and mass, charge state determination, deconvolution, identification of isotopic clusters, etc.). Connection between instrument interface 22 and mass spectrometer and/or ion source may be established by a wire or a glass fibre or wirelessly via radio communication.

The data processing device can be realized as a standard personal computer or in a distributed form with a number of processing devices interconnected by a wired or wireless network, so that the processor unit 23 may contain a plurality of processor cores in one or several interconnected units. The functions for processing the data are preferably implemented in an object-oriented programming language such as C# or C++; frameworks such as .NET may be used.

The storage unit 24 is adapted to store initial data vectors, e.g. measured mass spectra, and/or items of processed data, such as spectra with normalized intensity and/or calibrated mass scale, and/or items of additional data, e.g. the information in which database a spectral match for a particular initial data vector (or a corresponding processed data vector) was found. For this purpose, the storage unit preferably comprises memory devices which save information in the form of electrical charges, such as a random access memory, and/or memory devices which save information in the form of magnetic domains, such as a hard drive. Preferably, the storage unit 24 is adapted to store the initial data vectors, the items of processed data and/or the items of additional data in a relational database. A particularly preferred embodiment of a relational database will be described below in connection with FIG. 4. Preferably, the storage unit 24 comprises means for storing raw measurement data (from which the initial data vectors were derived) independently of the relational database; this could e.g. be in the form of individual files in a standard file system.

When the data processing device comprises visualization means 25 and interaction means 26, operation of the mass spectrometry setup is preferably controlled via a graphical user interface (GUI).

In proteomics experiments, the samples to be measured may comprise tissues from different organs or different body fluids; when labeling of the samples is performed, different tissues may be measured simultaneously in one mass spectrometry scan. The samples may be digested using e.g. trypsin; preferably they are ionized using a liquid chromatography-electrospray ion source and injected in a mass spectrometer. Preferably, additional stages of mass spectrometry ($MS^2$ or $MS''$) are carried out for interesting regions of the mass spectrum and/or selected elution time intervals.

Measured spectra may be structured via "studies" which contain in particular a list of spectra and additional information connected to a spectrum, in particular factors or study variables. Preferably, the measured spectra and items of additional data connected to a measured spectrum, e.g. the tissue from which the sample was taken, are saved in a database of the storage unit 24.

Figure 2:
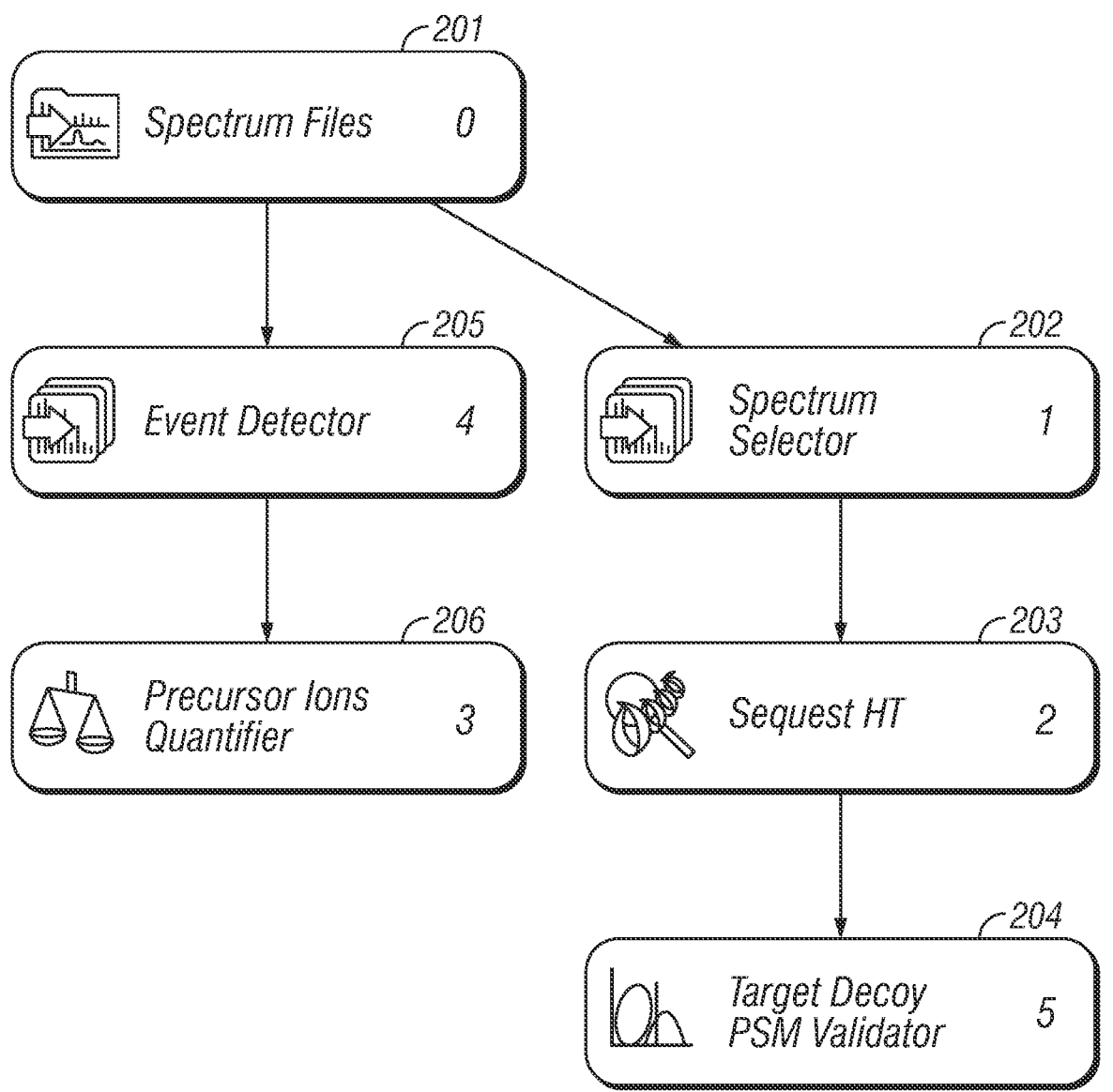
FIG. 2 shows an example of a first workflow to be carried out in a data processing device according to the invention.

Referring to FIG. 2, an example of a first workflow is shown in a GUI according to a particularly preferred embodiment of the invention. Processing steps are shown as boxes which are connected by arrows indicating the sequence of processing and the flow of information, wherein processed data from a particular step may be evaluated and/or modified by a subsequent processing step.

In step 201 ("Spectrum Files"), spectrum files are read from the storage unit. These files may contain one or more mass spectra in one or more mass ranges. When measured with a liquid chromatography-mass spectrometry setup, as is usually the case in proteomics, a number of mass spectra were measured at subsequent times, and the raw data thus contain both the information of a chromatogram, i.e. intensity against elution time, as well as that of a mass spectrum, i.e. intensity against mass-to-charge ratio. Preferably, the full set of data is kept in a separate raw file, and only the initial data vectors to be processed are extracted and stored in the database.

From the spectrum files, the mass spectra to be analyzed are selected in step 202 ("Spectrum Selector"). This may comprise a restriction to a certain mass range and/or a selection according to one or more items of additional data, e.g. only selecting spectra measured under specific conditions or prepared in a specific way. In particular, measured spectra may e.g. be selected according to the tissue they were taken from.

In some embodiments, the mass spectra may be processed further in order to reduce the amount of data; in particular, a peaklist may be generated containing a position and intensity, which can be determined from a centroid fitted to the measured spectra with a defined centre position and peak height.

In step 203 ("Sequest HT"), the selected mass spectra are compared to reference spectra in a database. When position and relative intensities of peaks in the measured spectrum match those of a reference spectrum from a known peptide or protein within a certain tolerance, it can be concluded that the sample contains a particular peptide or protein, i.e. that peptide or protein is identified. The reference spectrum may have been measured or calculated based on a digestion "in silico" of the protein e.g. by trypsin. For the identification of proteins and peptides, many different methods and/or databases are known; one method is e.g. disclosed by Cox et al. in J. Proteome Res. 2011, 10, 1794-1805.

For limiting the false discovery rate, in step 204 ("Target Decoy PSM Validator") a validation of the identified peptides or peptide spectral matches (PSM) is carried out. In particular, a threshold score may be defined, which has to be surpassed in order for an identification to be considered. This threshold score may e.g. be determined via a decoy search. In principle, other methods for a validation of the identification could also be used.

The spectrum files read in step 201 are also supplied to processing step 205 ("Event detector"). Processing steps in the workflow may preferably be implemented by dynamic modules, which generally can be processed concurrently. Step 205 serves to identify peaks which are well defined with respect to the time axis of elution time of the liquid chromatography setup and the mass axis of the mass spectrometer.

In step 206 ("Precursor Ions Quantifier"), the absolute or relative quantity of the measured samples is determined. Processing steps may use items of processed data from multiple processing steps. For step 206, position and intensity of detected peaks as well information on identified peptides and/or proteins are needed. As a result, step 206 needs to be carried out posterior to step 205 and step 204. When all steps are implemented as dynamic modules, modules 204 and 205 are concurrent, whereas module 206 needs to wait for both modules to finish processing. Quantification may be carried out according to known label-based or label-free methods, such as disclosed in WO 2013/149963 A1. In a label-based method, different mass tags are attached to originally identical peptides from different samples thus causing the occurrence of multiple peaks separated by the mass differences corresponding to the respective mass tag; by subsequently mixing different sub-samples and performing mass spectrometry, the influence of varying instrument response is automatically accounted for when comparing the intensities of the different peaks in order to determine relative quantities. When using e.g. the method of Stable Isotope Labeling by Amino acids in Cell culture (SILAC), cells are fed either normal ('light') or heavy amino acids in culture; in order to produce heavy amino acids, preferably $^{12}$C atoms are substituted by $^{13}$C atoms.

According to a preferred embodiment of the invention, items of processed and/or additional data produced or used in the processing of the first workflow are stored in one result file. The processing steps of the first workflow may in particular normalize the intensities and/or convert a mass scale of the initial data vectors processed, and generate intermediary results such as primary search results and raw quantification information, so that the first workflow can also be termed a "processing workflow".

An advantage of the inventive data processing device consists in that it is possible to store arbitrary items of data and to process arbitrary items of data, or to process other data based on those arbitrary items of data. For this purpose, the data storage unit comprises in a preferred embodiment of the invention a data interface for defining dynamic data types and/or modifying the relational database, so that dynamic tables can be added and/or columns can be added to existing dynamic tables. In a particularly preferred embodiment of the invention, the data processing device comprises a module interface, which allows for adding dynamic modules that implement processing steps of a workflow, wherein the dynamic modules can save and/or retrieve items of data as well as add dynamic data types and/or modify tables of the relational database. In the following, particularly these two aspects of the invention are described in more detail for some processing steps of a second workflow.

Figure 3:
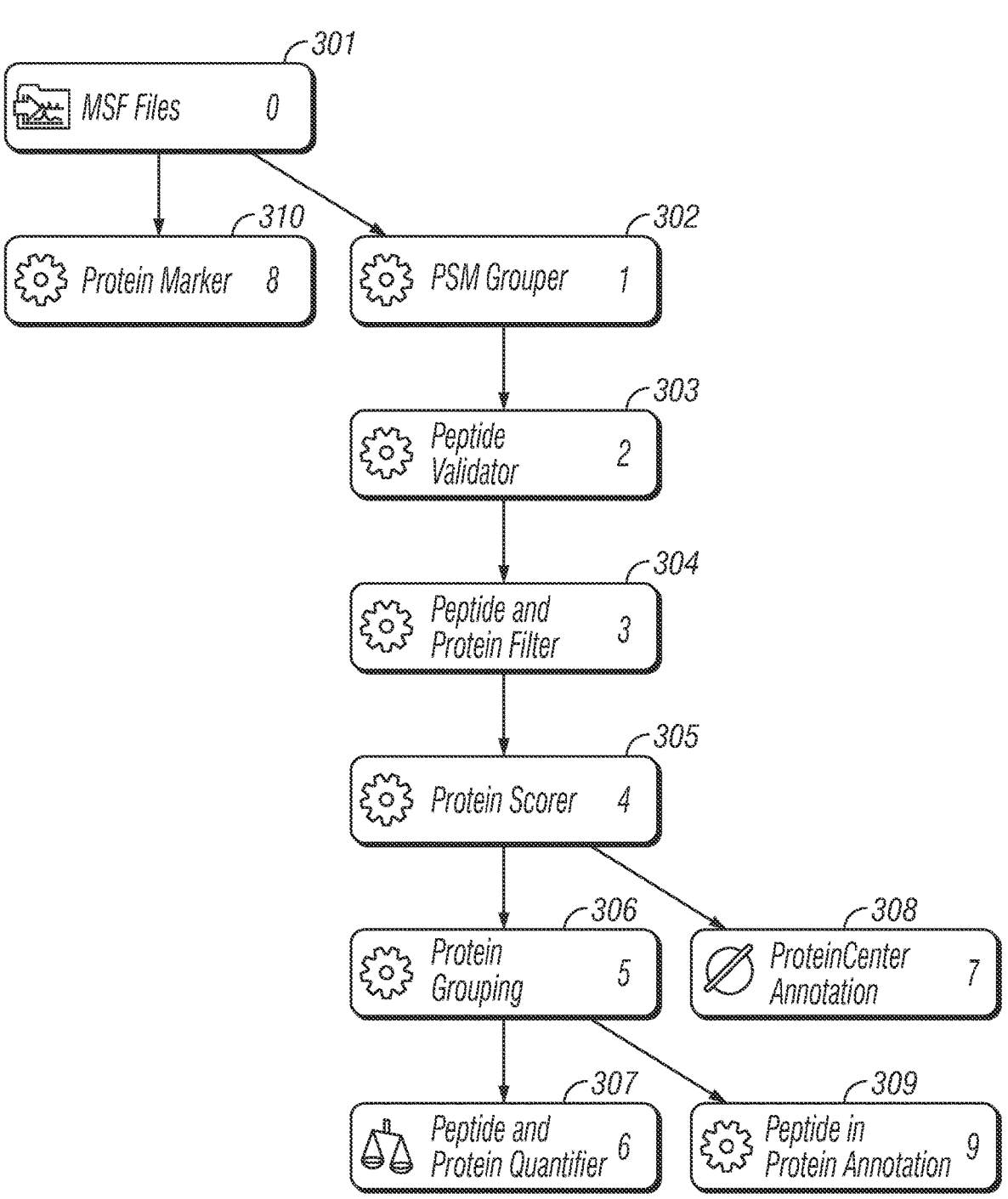
FIG. 3 shows an example of a second workflow to be carried out in a data processing device according to the invention.

In FIG. 3, an example of a second workflow is shown, wherein processing steps are depicted as boxes which are connected by arrows indicating the sequence of processing and the flow of information. The processing steps of the second workflow may in particular combine preliminary results from multiple processing steps of a first workflow into consensus peptides, proteins and quantification, so that the second workflow can also be termed a "consensus workflow".

Before discussing the processing steps, a data interface of the storage unit according to a preferred embodiment of the invention, also termed "Entity Data Service", will be described. The entity data service is preferably realized as an object-relational mapper, which can be used to persist objects and connections between objects in a relational database. The relational database can e.g. be implemented using a library such as SQLite, and the content of the database may be stored in a database file on a non-volatile memory such as a hard drive. In a particularly preferred embodiment, .NET classes are mapped to tables in the database file, so that each class is stored in a separate table in which each column represents a property and each row represents an object of a class. This has the advantage that persisted data can be read from the database file and converted back into collections of .NET objects.

It is preferred that the entity data service further stores meta information about the persisted objects, indicating how they should be handled and displayed. The meta information may comprise an ontology, in particular based on public standards, to facilitate e.g. processing mass spectra based on items of additional information.

Preferably, initial data vectors, processed data and additional data of a workflow are stored in one relational database, the contents of which can be persisted in a result file, in particular one database file or a set of associated files.

Figure 4A:
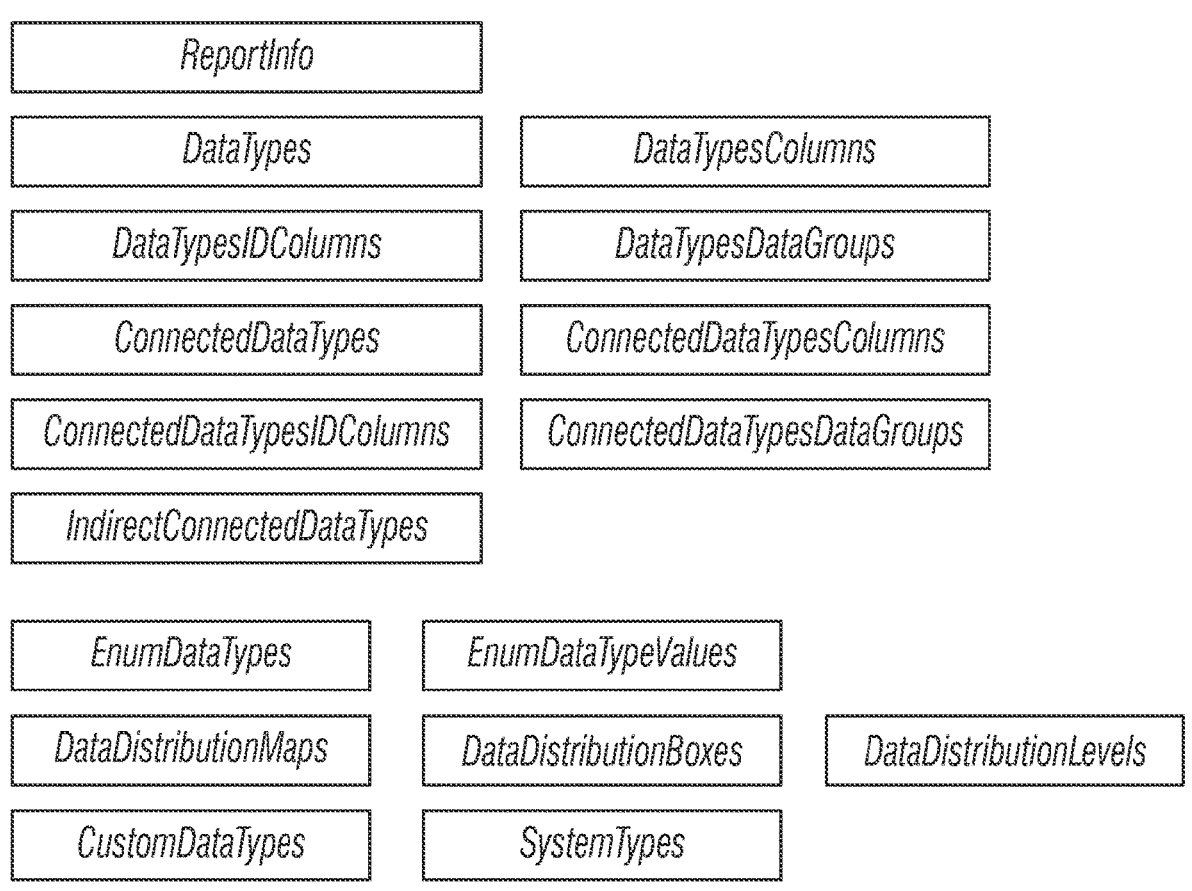
FIG. 4 shows an example of the tables contained in a database file; static tables are depicted in FIG. 4*a*), whereas dynamic tables are shown in FIG. 4*b*).
Figure 4B:
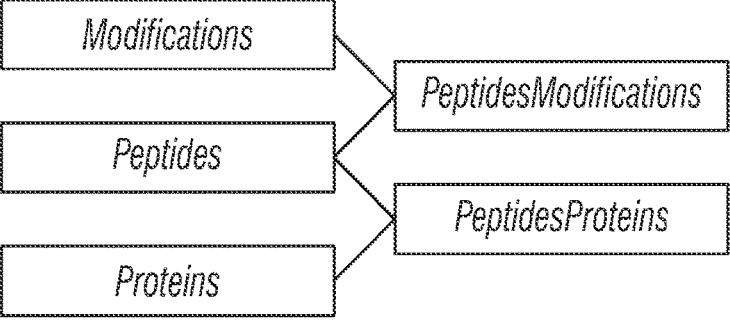

In FIG. 4, a schematic representation of the exemplary tables contained in a result file is shown; predefined tables—which are present in every result file and contain administrative information—are depicted in FIG. 4a), whereas dynamic tables are shown in FIG. 4b). According to a preferred embodiment of the present invention, the following tables are predefined:

In the table "ReportInfo" general information is stored, such as a date of creation of the result file and the version of the database engine used for creation of the database; preferably, a globally unique identifier is assigned to each created result file.

The table "DataTypes" contains a list of all dynamic data types defined in a static or dynamic program module or by the user. A dynamic data type consists of a set of properties, which can either be of one basic data type or (in the case of an object) be made up of a combination of basic data types. For each dynamic data type, a dynamic table is created for saving the data items of that data type. In the table "Data-Types", one row is stored for each defined dynamic data type; preferably, it contains a unique name, a display name, a description of the dynamic date type and the associated dynamic table for saving the data items or instances. Preferably, each dynamic data type is assigned a (globally) unique numeric identifier (GUID).

In the table "DataTypesColumns", the properties of a dynamic data type are indicated, comprising a description for each property of all defined dynamic data types. Preferably, properties can be defined as nullable, which defines that null values are allowed, or can be set to a default value if no specific value is given.

The table "DataTypesIDColumns" stores which properties are specified to comprise the unique numeric identifier (ID) of objects of a defined dynamic data type.

In the table "DataTypesDataGroups" a number of properties of dynamic data types may be given that can be clustered, allowing for grouping together a subset of columns of a dynamic data type. This allows e.g. for identifying which columns were created by a specific module implementing a specific processing step.

The table "CustomDataTypes" contains a list of all basic data types that can be used in the definition of dynamic data types or their properties. Table 1 gives a preferred list of supported basic data types, comprising string, double, int (especially Int 32), long (especially Int64), bool and byte (or array of bytes).

TABLE 1

| CustomDataTypes | |
|---|---|
| CustomDataType | BasicDataType |
| 1 | String |
| 2 | Double |
| 3 | Int |
| 4 | Long |
| 5 | Bool |
| 6 | Byte |

In the table "ConnectedDataTypes", connections between dynamic data types are listed, indicating further in which additional dynamic table the properties of the connection are stored; preferably, a unique name and/or numerical identifier is also given. Generally, many to many (m to n) connections between two dynamic data types are possible, and further properties of the connection can be stored. Advantageously, this allows for storing information that is not associated to one of the dynamic data types, but to the connection itself.

The table "ConnectedDataTypesColumns" lists the properties associated with the defined connections. For each additional item of data related to the connection, a further row is added to this table.

The table "ConnectedDataTypesIDColumns" stores which properties are specified to comprise the unique ID of connections between objects of dynamic data types.

In the table "ConnectedDataTypesDataGroups" a number of properties of a defined connection between dynamic data types may be given that can be clustered, allowing for grouping together a subset of columns that e.g. were created by a specific module implementing a specific processing step.

The table "IndirectConnectedData Types" allows for storing indirect connection; even though no connection is defined between a first and a second table, they may be connected via a third table, if both a connection between the first and the third table and a connection between the second and the third table exist. When both the first and the second table are also connected to a fourth table, two different paths for reading data from the second table based on data from the first table. In the table "IndirectConnectedDataTypes", a default connection path can be specified between the first table and the second table which are indirectly connected.

Preferably, columns of a defined dynamic data type may contain arbitrary data types, when a module for conversion is provided. The predefined table "SystemTypes" contains an indication which converter to use for reading or writing a specific column of a defined dynamic table. In a particularly preferred embodiment, a data processing device according to the invention may be implemented in programming language such as C# using a framework such as .NET, so that for each dynamic data type a C# class of a specific system type is defined, and for each property of the dynamic data type a converter for reading and storing can be used. The table "SystemTypes" then connects a unique identifier stored in the dynamic tables with the full name of the .NET class type of the converter.

The predefined table "EnumDataTypes" contains a list of specifically defined data types that consist of a set of named constants. In the table "EnumDataTypeValues", the different possible values of the respective enumeration are listed. Preferably, each enumeration constant is mapped to a unique integer value in order to speed up processing.

The predefined tables "DataDistributionMaps", DataDistributionBoxes" and "DataDistributionLevels" are connected with a special visualization shown in FIG. 6 and will be described below.

In principle, some of the predefined tables of the current embodiment, in particular the tables associated with the DataDistribution visualization, can be omitted without departing from the scope of the claims, so that the number of predefined tables in an alternative embodiment may differ.

FIG. 4b) shows a number of exemplary dynamic tables corresponding to the first workflow. Additional dynamic tables may be added at any time in a workflow when defined e.g. by a module implementing a processing step.

The dynamic table "Peptides" contains a list of peptides identified from a spectral match in a database. Properties of the dynamic data type Peptides are stored as additional columns in the dynamic table. These properties may in particular comprise a sequence and a charge.

In the dynamic table "Proteins", identified proteins are listed. Properties of the dynamic data type Proteins may comprise a sequence, a description and a weight.

The dynamic table "PeptidesProteins" lists connections between a protein and a peptide; a peptide is connected to a protein when it constitutes a building block of the protein. Preferably the position of the peptide in the protein is stored as a property of the respective connection.

The mass of a peptide may have been changed by substituting e.g. an hydrogen atom by a chemical group. In the dynamic table "Modifications" such modifications of a peptide are listed; the mass difference caused by the modification is preferably stored in an additional column.

Information on which peptide is modified by which chemical group is stored as a connection between a peptide and a modification in the dynamic table "PeptidesModifications". Properties of the connection may in particular comprise the position of the modification in the peptide.

Referring to FIG. 3, the results from a first workflow are read in step 301 ("MSF Files"). The items of information contained in the result file/s of the first workflow are in particular mass spectra (initial data vectors), identified peptides, proteins and modifications as well as quantification information. In the following, the second workflow will be described based on an example dataset. For simplicity, initial data vectors (i.e. mass spectra) and/or processed data vectors are omitted (not shown in the tables discussed below).

The static or dynamic module that implements processing step 301 is adapted to define the dynamic data types peptide, protein and modification. To illustrate basic principles more clearly, only selected properties of the dynamic data types are given with schematic values in the example dataset below. Table 2 shows the content of the predefined table DataTypes after definition of the dynamic data types.

TABLE 2

| DataTypes | | | | |
|---|---|---|---|---|
| DataTypeID | Name | TableName | DisplayName | Description |
| 1 | Peptide | Peptides | Peptides | Identified peptides |
| 2 | Protein | Proteins | Proteins | The proteins |
| 3 | Modification | Modifications | Modifications | Amino acid modifications |

In table 3, which shows the predefined table "Data TypeColumns", the properties of the defined data types are listed. For most of the properties, semantic information concerning the interpretation and/or processing of the respective property is given in addition to the information generally needed for the relational database. The semantic term "ID" refers to the unique numerical identifier or index used for the identification of the defined dynamic data type e.g. when retrieving information. Each peptide has a specific sequence of amino acids constituting the peptide, which is indicated by the semantic term "Sequence". As the data processing device is especially adapted for the processing of mass spectra, the semantic term "Monoisotopic Mass" and "Average Mass" are predefined. Further semantic terms defined especially for the application in proteomics are e.g. "SequestScore", indicating a score as to the degree of agreement between a measured spectrum and the identified peptide or protein, as well as "ProteinAccession". Semantic terms are preferably predefined based on generally accepted standard endorsed e.g. by the Human Proteome Organization; for an efficient implementation, a further translation e.g. via an additional table may be carried out.

TABLE 3

| DataTypeColumns | | | | |
|---|---|---|---|---|
| DataTypeID | ColumnName | DisplayName | CustomData Type | SemanticTerm |
| 1 | ID | Peptide ID | 3 | PeptideID |
| 1 | Sequence | Sequence | 1 | PeptideSequence |
| 1 | Mass | Monoisotopic mass | 2 | Monoisotopic Mass |
| 1 | XCorrScore | XCorrScore | 2 | SequestXCorrScore |
| 1 | RawQuanValue | Quan Value | 3 | PrecursorRawQuanValue |
| 1 | QuanChannel | Quan Channel | 3 | PrecursorQuanChannel |
| 2 | ID | Protein id | 3 | ProteinID |
| 2 | Sequence | Protein sequence | 1 | ProteinSequence |
| 2 | Accession | Accession | 1 | ProteinAccession |
| 2 | TitleLine | Title line | 1 | FastaTitleLine |
| 3 | ID | Modification Id | 3 | ModificationID |
| 3 | Name | Name | 1 | ModificationName |
| 3 | AverageMass | Av mass | 2 | AverageMass |
| 3 | MonoisoMass | Monoiso mass | 2 | MonoiotopicMass |

When analyzing mass spectra in proteomics, there is a connection between identified proteins and identified peptides: the position of the peptide in the protein. Further, a peptide may be modified, resulting in a mass difference from the unchanged peptide. The modification is located at a certain position in the peptide, and this position is preferably stored as a property of the connection between peptide and modification. Table 4 shows the predefined table "ConnectedDataTypes" with a list of the connected dynamic data types, and table 5 shows the predefined table "ConnectedDataTypesColumns" that gives the properties associated with connections (in the current case the position of a modification in the sequence of a peptide).

TABLE 4

| ConnectedDataTypes | | |
|---|---|---|
| DataTypeID1 | DataTypeID2 | ConnectedTableName |
| 1 | 2 | PeptidesProteins |
| 1 | 3 | PeptidesModifications |

TABLE 5

| | | ConnectedDataTypesColumns | | | |
|---|---|---|---|---|---|
| DataTypeID1 | DataTypeID2 | ColumnName | DisplayName | CustomData Type | SemanticTerms |
| 1 | 3 | Position | Amino acid position | 3 | SequencePosition |

In table 6, the dynamic table "Peptides" is shown with schematic values for the sequence of peptides identified in the first workflow, indicating also the score of the identification, e.g. the degree of agreement of the measured spectrum with a database spectrum. Preferably, tables do not need to be normalized, so that not only the sequence (and if present, a modification of a specific peptide, see below) but also the mass of the peptide is given.

TABLE 6

| | | Peptides | | | |
|---|---|---|---|---|---|
| ID | Sequence | Mass | Score | RawQuanValue | QuanChannel |
| 1 | ABC | 100 | 1.1 | 2000 | 1 |
| 2 | ABC | 105 | 2.3 | 2100 | 2 |
| 3 | ABCD | 110 | 1.5 | 3000 | 1 |
| 4 | ABCD | 110 | 2 | 3500 | 1 |

Proteins identified in the first workflow are listed in the dynamic table "Proteins" shown in table 7. In addition to the sequence, the accession or identifier in a protein database is also indicated; the accession is also given in the FASTA format.

TABLE 7

| | | Proteins | |
|---|---|---|---|
| ID | Sequence | Accession | TitleLine |
| 1 | 123ABC4567 | Accession1 | >g1 Accession1 |
| 2 | 098ABC765432 | Accession2 | >g1 Accession2 |

Connections between peptides and proteins, indicating which identified peptides are present in an identified protein, are listed in the dynamic table "PeptidesProteins" shown in table 8. In principle, this table could comprise further columns with additional data, containing e.g. the position of the respective peptide in the protein.

TABLE 8

| PeptidesProteins | |
|---|---|
| PeptidesID | ProteinsID |
| 1 | 1 |
| 1 | 2 |
| 2 | 1 |
| 2 | 2 |
| 3 | 2 |
| 4 | 2 |

In one or several positions in the peptide, an atom (in particular a hydrogen atom) may be substitudes e.g. by a functional group. Such a modification is listed in the dynamic table "Modifications" shown in table 9.

TABLE 9

| | Modifications | | |
|---|---|---|---|
| ID | Name | AverageMass | MonoisoMass |
| 1 | Acetyl | 5 | 4.9 |

The position of the modification in the peptide is preferably stored as a connection between peptide and modification, given in the dynamic table "PeptidesModifications" shown in table 10.

TABLE 10

| PeptidesModifications | | |
|---|---|---|
| PeptidesID | ModificationsID | Position |
| 2 | 1 | 2 |

A workflow may contain concurrent processing steps, which may be carried out in arbitrary order. For the second workflow of FIG. 3, e.g. steps 310 and 302 are concurrent. In the following discussion, step 310 is performed first.

Step 310 ("Protein Marker") serves to identify protein matches which are caused by a contamination. In this step, one or more databases, in particular FASTA files, are searched for matches with the proteins read from the first workflow. The module carrying out this processing step is adapted to either add a further column of type bool for each database searched or to add one column containing a list of databases which gave a match. In table 11, the changed predefined table "DataTypeColumns" is shown (cf. Table 3), indicating that a column has been added to the dynamic table "Proteins".

TABLE 11

| | | | CustomData | |
|---|---|---|---|---|
| DataTypeID | ColumnName | DisplayName | Type | SemanticTerm |
| 1 | ID | Peptide ID | 3 | PeptideID |
| 1 | Sequence | Sequence | 1 | PeptideSequence |
| 1 | Mass | Monoisotopic mass | 2 | monoisotopic mass |
| 1 | XCorrScore | XCorrScore | 2 | SequestXCorrScore |
| 1 | RawQuanValue | Quan Value | 3 | PrecursorRawQuanValue |
| 1 | QuanChannel | Quan Channel | 3 | PrecursorQuanChannel |
| 2 | ID | Protein id | 3 | ProteinID |
| 2 | Sequence | Protein sequence | 1 | ProteinSequence |
| 2 | Accession | Accession | 1 | ProteinAccession |
| 2 | TitleLine | Title line | 1 | FastaTitleLine |
| 3 | ID | Modification Id | 3 | ModificationID |
| 3 | Name | Name | 1 | ModificationName |
| 3 | AverageMass | Av mass | 2 | AverageMass |
| 3 | MonoisoMass | Monoiso mass | 2 | Monoisotopic Mass |
| 2 | IsContaminant | Is contaminant | 5 | IsContaminantFlag |

Table 12 shows the changed dynamic table "Proteins" (cf. Table 7), comprising the column which indicates if the respective protein was found in a contaminant database.

TABLE 12

Proteins

| ID | Sequence | Accession | TitleLine | IsContaminant |
|---|---|---|---|---|
| 1 | 123ABC4567 | Accession1 | >g1 Accession1 | FALSE |
| 2 | 098ABC765432 | Accession2 | >g1 Accession2 | TRUE |

By this additional information, it is now possible in subsequent processing steps to select mass spectra and/or identified proteins, which did not result in a match in any contaminant database and thus should be further analyzed.

In step 302 ("PSM Grouper"), identified peptides or peptide spectral matches (PSMs) are grouped. Preferably, the dynamic module for grouping peptides sorts the peptides both according to sequence and to mass, because modifications may lead to different masses in spite of the same sequence. For grouping the peptides, a new dynamic data type "PeptideGroup" is added to the predefined table "Data-Types", as shown in table 13.

TABLE 13

DataTypes

| DataTypeID | Name | TableName | DisplayName | Description |
|---|---|---|---|---|
| 1 | Peptide | Peptides | Peptides | Identified peptides |
| 2 | Protein | Proteins | Proteins | The proteins |
| 3 | Modification | Modifications | Modifications | Amino acid modifications |
| 4 | PeptideGroup | PeptideGroups | Peptide groups | Grouped peptides |

In addition to a unique id of the peptide group, the sequence and mass are also stored, as indicated in the changed predefined table "DataTypeColumns" shown in table 14.

TABLE 14

DataTypeColumns

| | | | CustomData | |
|---|---|---|---|---|
| DataTypeID | ColumnName | DisplayName | Type | SemanticTerm |
| 1 | ID | Peptide ID | 3 | PeptideID |
| 1 | Sequence | Sequence | 1 | PeptideSequence |
| 1 | Mass | Monoisotopic mass | 2 | monoisotopic mass |
| 1 | RawQuanValue | Quan Value | 3 | PrecursorRawQuanValue |
| 1 | QuanChannel | Quan Channel | 3 | PrecursorQuanChannel |
| 1 | XcorrScore | XcorrScore | 2 | SequestXCorrScore |
| 2 | ID | Protein ID | 3 | ProteinID |
| 2 | Sequence | Protein sequence | 1 | ProteinSequence |
| 2 | Accession | Accession | 1 | ProteinAccession |
| 2 | TitleLine | Title line | 1 | FastaTitleLine |
| 3 | ID | Modification ID | 3 | ModificationID |
| 3 | Name | Name | 1 | ModificationName |
| 3 | AverageMass | Av mass | 2 | AverageMass |

TABLE 14-continued

| DataTypeColumns | | | | |
|---|---|---|---|---|
| DataTypeID | ColumnName | DisplayName | CustomData Type | SemanticTerm |
| 3 | MonoisoMass | Monoiso mass | 2 | MonoisotopicMass |
| 2 | IsContaminant | Is contaminant | 6 | IsContaminantFlag |
| 4 | ID | Peptide group ID | 3 | PeptideGroupID |
| 4 | Sequence | Sequence | 1 | PeptideGroupSequence |
| 4 | Mass | MonoIsotopic mass | 2 | Monoisotopic mass |

In the predefined table "ConnectedDataTypes", the newly defined connections between peptides, proteins, peptide groups and modifications are indicated, as can be seen in table 15.

TABLE 15

| ConnectedDataTypes | | |
|---|---|---|
| DataTypeID1 | DataTypeID2 | ConnectedTableName |
| 1 | 2 | PeptidesProteins |
| 1 | 3 | PeptidesModifications |
| 1 | 4 | PeptidesPeptideGroups |

Table 16 shows a schematic example of a dynamic table with peptide groups; in case of a modification, two peptides with the same sequence are classed in different groups. The assignment of peptides to groups is stored as a connection; the corresponding connections are shown in table 17.

TABLE 16

| PeptideGroups | | |
|---|---|---|
| ID | Sequence | Mass |
| 1 | ABC | 100 |
| 2 | ABC | 105 |
| 3 | ABCD | 110 |

TABLE 17

| PeptidesPeptideGroups | |
|---|---|
| PeptidesID | PeptideGroupsID |
| 1 | 1 |
| 2 | 2 |
| 3 | 3 |
| 4 | 3 |

In step 303 ("Peptide Validator"), peptide groups are validated, so that a score or confidence is associated with a found peptide group. For this, a new column "Confidence" is added to the dynamic table "PeptideGroups" as is reflected by the new row in the predefined table "Data-TypeColumns" shown in table 18. An exemplary list of peptide groups is shown in table 19.

TABLE 18

| DataTypeColumns | | | | |
|---|---|---|---|---|
| DataTypeID | ColumnName | DisplayName | CustomData Type | SemanticTerm |
| 1 | ID | Peptide ID | 3 | PeptideID |
| 1 | Sequence | Sequence | 1 | PeptideSequence |
| 1 | Mass | Monoisotopic mass | 2 | monoisotopic mass |
| 1 | XCorrScore | XcorrScore | 2 | SequestXCorrScore |
| 1 | RawQuanValue | Quan Value | 3 | PrecursorRawQuanValue |
| 1 | QuanChannel | Quan Channel | 3 | PrecursorQuanChannel |
| 2 | ID | Protein ID | 3 | ProteinID |
| 2 | Sequence | Protein sequence | 1 | ProteinSequence |
| 2 | Accession | Accession | 1 | ProteinAccession |
| 2 | TitleLine | Title line | 1 | FastaTitleLine |
| 3 | ID | Modification ID | 3 | ModificationID |
| 3 | Name | Name | 1 | ModificationNaame |
| 3 | AverageMass | Av mass | 2 | AverageMass |
| 3 | MonoisoMass | Monoiso mass | 2 | MonoisotopicMass |
| 2 | IsContaminant | Is contaminant | 6 | IsContaminantFlag |
| 4 | ID | Peptide group ID | 3 | PeptideGroupID |
| 4 | Sequence | Sequence | 1 | PeptideGroupSequence |
| 4 | Mass | MonoIsotopic mass | 2 | Monoisotopic mass |
| 4 | Confidence | Confidence | 3 | PeptideGroupConfidence |

TABLE 19

| PeptideGroups | | | |
|---|---|---|---|
| ID | Sequence | Mass | Confidence |
| 1 | ABC | 100 | 3 |
| 2 | ABC | 105 | 3 |
| 3 | ABCD | 110 | 2 |

In step 304 ("Peptide and Protein Filter"), the lists of identified peptides and proteins are filtered based on a threshold of the confidence, so that only peptides and/or peptide groups and/or proteins which are identified with sufficient reliability will be taken into account. Additionally or alternatively, the filtering may be carried out so that known contaminants are not processed any further. Further, filtering may be based on additional information such as the tissue the sample was taken from. Newly defined dynamic data types are shown in table 20.

TABLE 20

| DataTypeID | ColumnName | DisplayName | CustomData Type | SemanticTerm |
|---|---|---|---|---|
| 1 | ID | Peptide ID | 1 | PeptideID |
| 1 | Sequence | Sequence | 1 | PeptideSequence |
| 1 | Mass | Monoisotopic mass | 2 | monoisotopic mass |
| 1 | XcorrScore | XcorrScore | 2 | SequestXcorrScore |
| 1 | RawQuanValue | Quan Value | 3 | PrecursorRawQuanValue |
| 1 | QuanChannel | Quan Channel | 3 | PrecursorQuanChannel |
| 1 | ExcludedBy | Excluded By | 3 | ExclusionState |
| 2 | ID | Protein ID | 1 | ProteinID |
| 2 | Sequence | Protein sequence | 1 | ProteinSequence |
| 2 | Accession | Accession | 1 | ProteinAccession |
| 2 | TitleLine | Title line | 1 | FastaTitleLine |
| 3 | ID | Modification ID | 1 | ModificationID |
| 2 | ExcludedBy | Excluded By | 3 | ExclusionState |
| 3 | Name | Name | 1 | ModificationName |
| 3 | AverageMass | Av mass | 2 | AverageMass |
| 3 | MonoisoMass | Monoiso mass | | MonoisotopicMass |
| 2 | IsContaminant | Is contaminant | 6 | IsContaminantFlag |
| 4 | ID | Peptide group ID | 3 | PeptideGroupID |
| 4 | Sequence | Sequence | 1 | PeptideGroupSequence |
| 4 | Mass | MonoIsotopic mass | 2 | Monoisotopic mass |
| 4 | Confidence | Confidence | 3 | PeptideGroupConfidence |
| 4 | ExcludedBy | Excluded By | 3 | ExclusionState |

For the dynamic data types peptide, protein and peptide group an exclusion state is added as a property. Preferably, the corresponding column is filled with a special value such as −1 in order to indicate that the corresponding element or row is not excluded; when a module implementing processing step n marks a row for exclusion, in particular the number n of the processing step and/or the module is used to indicate that this element is to be excluded.

In an alternative embodiment of the present invention, a property for the exclusion state is added on or before step 301, so that any module in the workflow may change the content of the column in order to filter out undesired peptides and/or proteins.

Table 21 shows a list of the peptides identified in the example workflow; the peptides in the first and the second row are still processed, whereas the third and fourth row are filtered out.

TABLE 21

| ID | Sequence | Mass | Score | RawQuan Value | Quan Chan | Excluded By |
|---|---|---|---|---|---|---|
| 1 | ABC | 100 | 1.1 | 2000 | 1 | −1 |
| 2 | ABC | 105 | 2.3 | 2100 | 2 | −1 |
| 3 | ABCD | 110 | 1.5 | 3000 | 1 | 5 |
| 4 | ABCD | 110 | 2 | 3500 | 1 | 5 |

In table 22 a list of identified proteins is given; for the current example, the protein in the first row is excluded.

TABLE 22

| | | | Proteins | | |
|---|---|---|---|---|---|
| ID | Sequence | Accession | TitleLine | IsContaminant | ExcludedBy |
| 1 | 123ABC4567 | Accession1 | >gl Accession1 | FALSE | 5 |
| 2 | 098ABC765432 | Accession2 | >gl Accession2 | TRUE | −1 |

Table 23 shows the corresponding list of peptide groups; due to the higher confidence level, the first and the second row are processed, whereas the third row is filtered out.

TABLE 23

| Peptide Groups ID | Sequence | Mass | ExdudedBy | Confidence |
|---|---|---|---|---|
| 1 | ABC | 100 | −1 | 3 |
| 2 | ABC | 105 | −1 | 3 |
| 3 | ABCD | 110 | 5 | 2 |

Step 305 ("Protein Scorer") serves to add a further score to an identified protein, whereas in step 306 ("Protein Grouping"), proteins and the peptides contained in the proteins are grouped. For simplicity, these two processing steps will not be described in detail, and the corresponding new columns and/or dynamic tables are omitted.

In step 307 ("Peptide and Protein Quantifier") normalized quantification data is calculated based on raw quantification data from the first workflow and/or previous processing steps. When using e.g. SILAC for quantification, measured intensity of heavy amino acids is compared to the measured intensity of "light" amino acids. For this purpose, an additional column "HeavyLightRatio" is added to the dynamic tables containing peptides, proteins and peptide groups. Newly defined properties of dynamic data types are shown in table 24.

TABLE 24

| | | DataTypeColumns | | |
|---|---|---|---|---|
| DataTypeID | ColumnName | DisplayName | CustomData Type | SemanticTerm |
| 1 | ID | Peptide ID | 1 | PeptideID |
| 1 | Sequence | Sequence | 1 | PeptideSequence |
| 1 | Mass | Monoisotopic mass | 2 | monoisotopic mass |
| 1 | XcorrScore | XcorrScore | 2 | SequestXcorrScore |
| 1 | RawQuanValue | Quan value | 2 | PrecursorRawQuanValue |
| 1 | QuanChannel | Quan channel | 3 | PrecursorQuanChannel |
| 1 | ExcludedBy | Excluded By | 3 | ExclusionState |
| 2 | ID | Protein ID | 1 | ProteinID |
| 2 | Sequence | Protein sequence | 1 | ProteinSequence |
| 2 | Accession | Accession | 1 | ProteinAccession |
| 2 | TitleLine | Title line | 1 | TitleLine |
| 3 | ID | Modification ID | 1 | ModificationID |
| 2 | ExcludedBy | Excluded By | 3 | ExclusionState |
| 3 | Name | Name | 1 | ModificationName |
| 3 | AverageMass | Av mass | 2 | AverageMass |
| 3 | MonoisoMass | Monoiso mass | 2 | MonoisotopicMass |
| 3 | IsContaminant | Is contaminant | 6 | IsContaminantFlag |
| 4 | ID | Peptide group ID | 3 | PeptideGroupID |
| 4 | Sequence | Sequence | 1 | Sequence |
| 4 | Mass | MonoIsotopic mass | 2 | Monoisotopic mass |
| 4 | ExcludedBy | Excluded By | 3 | ExclusionState |
| 4 | Confidence | Confidence | 3 | PeptideGroupConfidence |
| 1 | HeavyLightRatio | Heavy/Light | 2 | PsmQuanRatio |
| 2 | HeavyLightRatio | Heavy/Light | 2 | ProteinQuanRatio |
| 3 | HeavyLightRatio | Heavy/Light | 2 | PeptideGroupQuanRatio |

Table 25 shows a list of exemplary identified peptides with added quantification ratios. Depending on the implementation, calculation of these ratios may be omitted for excluded peptides in order to speed up processing.

TABLE 25

| | | | | | | | Heavy |
|---|---|---|---|---|---|---|---|
| ID | Se-quence | Mass | RawQuan ScoreValue | Quan Chan | Excluded By | Light Ratio |
| 1 | ABC | 100 | 1.1 | 2000 | 1 | −1 | 1.5 |
| 2 | ABC | 105 | 2.3 | 2100 | 2 | −1 | 1.5 |
| 3 | ABCD | 110 | 1.5 | 3000 | 1 | 5 | 2 |
| 4 | ABCD | 110 | 2 | 3500 | 1 | 5 | 3 |

In table 26, a list of identified proteins with calculated quantification ratios is shown. For faster processing, calculation of these ratios may be omitted for excluded proteins.

TABLE 26

Proteins

| ID | Sequence | Accession | TitleLine | IsContaminant | Excluded By | HeavyLight Ratio |
|---|---|---|---|---|---|---|
| 1 | 123ABC4567 | Accession1 | >g1 Accession1 | FALSE | 5 | 1.5 |
| 2 | 098ABC765432 | Accession2 | >g1 Accession2 | TRUE | −1 | 2 |

Preferably, quantification ratios are also calculated for peptide groups; table 27 shows an exemplary list.

TABLE 27

| Peptide Groups ID | Sequence | Mass | Excluded By | Confidence | Heavy Light Ratio |
|---|---|---|---|---|---|
| 1 | ABC | 100 | −1 | 3 | 1.5 |
| 2 | ABC | 105 | −1 | 3 | 1.5 |
| 3 | ABCD | 110 | 5 | 2 | 3 |

Step 308 ("ProteinCenter Annotation") serves to receive additional information from an external database; this could e.g. be the information that a particular protein is related to a specific function. Grouping spectra and/or identified peptides according to a specific function and/or further processing of the proteins connected to a specific function is possible. In this way a gene ontology linking proteins and functions of the cell may be built up. Both this processing step and step 309 ("Peptide in Protein Annotation") do not form part of a "standard" workflow for identifying and quantifying peptides and/or proteins and for simplicity will not be described further.

Preferably, identified and/or quantified peptides and proteins are visualized and/or outputted in an arbitrary format after finishing the second workflow.

For the following examples of grouping and/or selecting initial data vectors (i.e. spectra) and/or items of processed data (e.g. identified peptides and proteins), it is assumed that a plurality of samples from different tissues of an organism has been taken, and that each sample from a specific tissue has been labelled with the same mass tag of a multiplexed labelling method (such as iTRAQ or TMT). This allows for the simultaneous measurement of sub-samples from different tissues in one mass-spectrometry run and thus avoids e.g. quantification errors due to changes in the instruments sensitivity over time. In addition, samples from the different tissues may have been measured twice using different acquisition methods known in the art such as data-dependent acquisition (DDA) or intelligent data acquisition (IDA). Besides data dependent methods the techniques described here can as well applied to data independent (DIA) or targeted acquisition methods. If required, data sets generated from data independent acquisitions may be deconvoluted, e.g. as described in U.S. Pat. No. 8,481,924, to allow use of algorithms designed for data dependent analysis.

Corresponding measurements are e.g. disclosed by Bailey et al. in J. Proteome Res. 13, 2152-2161 (2014). The result file for these measurements contains the spectra (initial data vectors), the tissue and the "channel" of the multiplexed labelling as well as the data acquisition method used (items of additional data).

Figure 5:
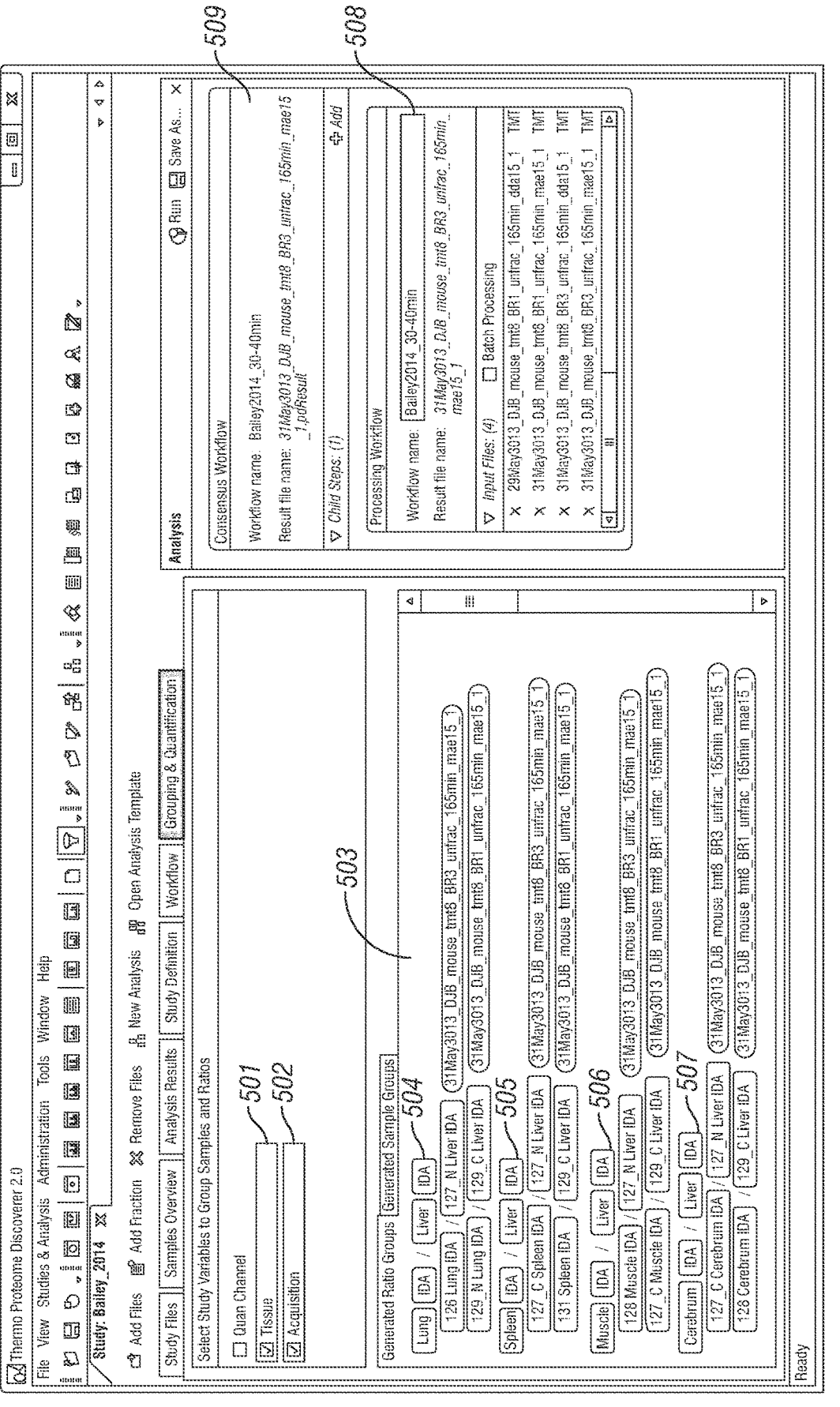
FIG. 5 shows an example of grouping initial data vectors and/or items of processed data according to items of additional data.

FIG. 5 shows an example of grouping initial data vectors and/or items of processed data according to items of additional data in a graphical user interface according to a particularly preferred embodiment of the invention.

Checkbox 501 allows for the user to indicate that the measured data are to be grouped according to the tissue of the sample.

In Checkbox 502, the user may indicate that the measured data are to be grouped according to the acquisition method used.

Window 503 contains a list of ratio groups for which a quantification giving ratios between peaks corresponding to differently labelled amino acids will be carried out. Because both checkbox 501 and checkbox 502 are activated, ratio groups of the different tissues sorted according to the acquisition method will be calculated.

Elements 504 to 507 indicate some of the created ratio groups.

Element 504 shows that the intensity ratio of peaks corresponding to peptides and/or proteins measured from a sample containing lung tissue and from a sample containing liver tissue will be calculated. In other words: peak intensities or peak areas will be calculated for the sample group lung (and acquisition method IDA) and for the sample group liver (and acquisition method IDA), and the ratio of these peak intensities or areas will be determined. The ratio for a protein or a peptide group containing several peptides is preferably calculated based on the median of the ratios for individual peptides. Additionally, element 504 comprises a list of corresponding input files containing raw data and/or initial data vectors.

Element 505 shows from which initial data vectors the intensity ratio for samples from the tissues spleen and liver will be calculated; accordingly, element 506 shows the files of measurements evaluated for the ratio between muscle and liver and element 507 indicated the initial data vectors for calculating the ratio between cerebrum and liver. The number of ratio groups depends from the number of different tissues measured in total; further ratio groups are omitted for simplicity.

The first processing workflow and the corresponding input files/initial data vectors are indicated in element 508; according element 509 shows the second workflow carried out.

In the first workflow, "raw" quantification information is calculated; depending on the labelling and/or quantification method used, the intensities of reporter peaks or the integrated areas of precursor ions are determined. The second workflow then contains a processing step of grouping the initial data vectors and/or items of processed data according to the activated checkboxes and to calculate intensity ratios from the grouped spectra.

Preferably, a list of all identified proteins is created in the second workflow, indicating further in which sample group, individual sample and/or file containing raw data and/or initial data vectors the respective protein was found.

Figure 6:
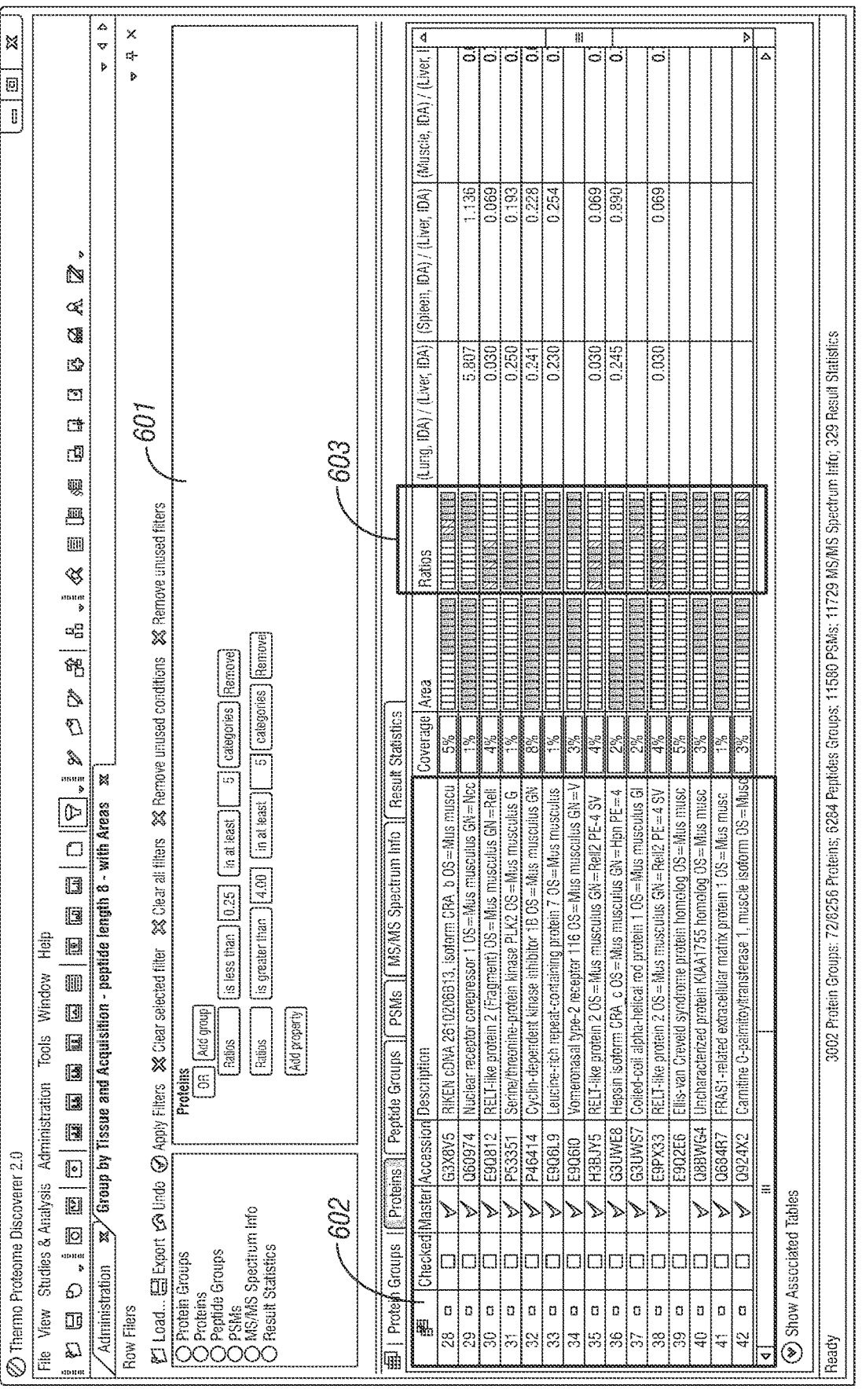
FIG. 6 shows an example of selecting initial data vectors and/or items of processed data according to items of additional data.

FIG. 6 shows an example of selecting initial data vectors and/or items of processed data according to items of additional data in a graphical user interface according to a particularly preferred embodiment of the invention.

Window 602 shows a list of identified proteins comprising their accession and a description.

Element 603 is a data distribution box indicating the ratio determined for the protein corresponding to the respective row in the sample group corresponding to the respective column; the ratio may be indicated by a colour code, a greyscale or a number. Preferably, the boxes are left white or empty when no ratio is defined because the protein was not found in one or both of the corresponding sample groups.

Data distribution boxes are preferably implemented as an array containing numeric values of double precision, integer or Boolean type. In particular, they may be implemented using several predefined tables shown in FIG. 4a):

The table "DataDistributionMaps" defines what each array box means; it contains a unique identifier, a name and the CustomDataType of the values given in a box. Optionally, a minimum and a maximum allowed value may be defined.

The boxes of the map are listed in the table "DataDistributionBoxes"; it contains a unique identifier of the box, a unique identifier of the map, a DisplayName and a description.

In the table "DataDistributionLevels" different levels are defined for the boxes.

Window 601 shows a graphical user interface for selecting proteins according to the calculated ratios; in the current example, only proteins showing a four-fold change of intensity ratio in at least five sample groups are shown.

Advantageously, the entity data service allows for selecting and/or grouping initial data vectors and/or items of processed data according to one or more items of additional data such as a calculated ratio.

As used herein, including in the claims, unless the context indicates otherwise, singular forms of the terms herein are to be construed as including the plural form and vice versa.

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language)

provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

What is claimed is:

1. A mass-spectrometric molecular compound identification system, comprising a processor unit adapted to process a plurality of mass spectrometry data sets provided by a mass spectrometer from a plurality of samples introduced into the mass spectrometer, each mass spectrometry data set comprising value pairs of measured intensity versus mass or mass over charge, a spectrum over a defined frequency range or a transient given over a defined time span, the processing comprising adjusting a mass scale, normalizing the intensity and/or identifying a compound corresponding to items of processed data, the items of processed data comprising processed mass spectrometry data sets and/or identifications of compounds, a storage unit adapted to save and retrieve the mass spectrometry data sets and/or the items of processed data, and items of additional data, the items of additional data comprising properties of the samples introduced in the mass spectrometer that are study variables, wherein each saved item of additional data or each saved item of processed data and each saved item of additional data is connected to at least one saved mass spectrometry data set, the at least one saved mass spectrometry data set to be retrievable as sets of corresponding data items, wherein the processor unit is adapted to group, select and/or modify mass spectrometry data and/or items of processed data according to one or more of the properties of the samples saved in the storage unit as saved items of additional data, retrieval, by the storage unit, of the mass spectrometry data and/or items of processed data is based on the one or more properties of the samples as set of corresponding data items, and wherein the storage unit is adapted to store the mass spectrometry data, the items of processed data and/or the items of additional data in a relational database and is comprising a data interface for defining dynamic data types in the relational database and/or modifying the relational database, so that dynamic tables can be added and/or columns can be added to existing dynamic tables, and an instrument interface communicatively coupled to a mass spectrometer, wherein the processor unit is further adapted to instruct the storage unit to retrieve a first subset of processed data based on a first study variable and a second subset of processed data based on a second study variable, to calculate intensity ratios of peaks from the first subset of processed data and of peaks from the second subset of processed data, and provide a visualization of a comparison of the first subset of processed data and the second subset of processed data;

wherein the processor unit is further adapted to (a) receive a first mass spectrometry data set generated by the mass spectrometer;

(b) analyze the first mass spectrometry data set to determine at least one measurement parameter adjustment based on one or more calculated characteristics of the first mass spectrometry data set;

(c) generate and transmit, through the instrument interface, one or more modified acquisition commands implementing the measurement parameter adjustment to the mass spectrometer; and (d) cause the mass spectrometer to acquire a second mass-spectrometry data set under the modified acquisition commands, and process the second data set together with the first data set for compound identification and visualization.

2. The mass-spectrometric molecular compound identification system of claim 1, wherein each mass spectrometry data set is assigned a unique identifier, and wherein each item of processed data is connected to an item of processed data from a preceding processing step of the same mass spectrometry data set and/or directly to the mass spectrometry data set.

3. The mass-spectrometric molecular compound identification system of claim 1, wherein the relational database comprises a fixed number of predefined tables and a number of dynamic tables, wherein at least one of the predefined tables contains a definition of dynamic data types, and wherein one dynamic table is created for each dynamic data type.

4. The mass-spectrometric molecular compound identification system of claim 1, wherein the definition of dynamic data types may comprise references to converters, wherein the processor unit is further adapted to convert a storage form of an item of the defined dynamic data type into a processing form when the storage unit retrieves the data, and the processor unit is further adapted to convert the processing form of an item of the defined dynamic data type into the storage form prior to the storage unit saving the data.

5. The mass-spectrometric molecular compound identification system of claim 1, wherein the storage unit is adapted to store connections between items of a first and items of a second dynamic data type, and wherein the relational database comprises at least one further dynamic table containing the connections between the items of the first and the items of the second dynamic data type.

6. The mass-spectrometric molecular compound identification system of claim 5, wherein the processor unit is adapted to create one dynamic table for each connection between two dynamic data types, and wherein the dynamic table of a connection contains one or more columns for storing items of additional data and/or items of processed data.

7. The mass-spectrometric molecular compound identification system of claim 1, wherein at least one of the dynamic data types is adapted for the characterization of the sample and/or a targeted compound.

8. The mass-spectrometric molecular compound identification system of claim 7, wherein, when the plurality of samples introduced into the mass spectrometer contain proteins and/or peptides and the dynamic data types comprise protein or peptide, the processor unit is further adapted to identify proteins, and the storage unit is adapted to store a table of identified proteins or a table of identified peptides in the relational database.

9. The mass-spectrometric molecular compound identification system of claim 7, wherein, the user-defined data types including drug, metabolite, and modification is indicative of the plurality of samples introduced into the mass spectrometer contain a drug and/or a metabolite.

10. The mass-spectrometric molecular compound identification system of claim 1, further comprising a module interface, which allows for adding dynamic modules that implement processing steps, wherein the dynamic modules can save and/or retrieve items of data as well as add dynamic data types and/or modify tables of the relational database.

11. The mass-spectrometric molecular compound identification system of claim 10, the mass-spectrometric molecular compound identification system further comprising a workflow interface for defining sequences of processing steps, wherein processing steps can be performed by default modules and/or dynamic modules, wherein the workflow interface provides services to modules which allows them to retrieve data from the relational database, define dynamic data types, and to save data in the relational database.

12. The mass-spectrometric molecular compound identification system of claim 11, wherein the workflow interface is adapted to define a first and a second workflow, each workflow comprising a sequence of one or more processing steps, wherein the first workflow is carried out by the processor unit before the second workflow, and wherein the processed data from the first workflow is used as input data for the second workflow.

13. The mass-spectrometric molecular compound identification system of claim 12, wherein the workflow interface is adapted to define a number of first workflows, each workflow comprising a sequence of one or more processing steps, wherein the first workflows are carried out independently by the processor unit, and wherein the second workflow comprises a processing step of combining, comparing and/or analyzing the processed data resulting from the number of first workflows.

14. The mass-spectrometric molecular compound identification system of claim 10, wherein the mass-spectrometric molecular compound identification system is adapted to store a workflow comprising a sequence of processing steps in a workflow file, and wherein the mass-spectrometric molecular compound identification system is further adapted to store at least the items of processed data, from a workflow being carried out by the processor unit in a result file.

15. The mass-spectrometric molecular compound identification system of claim 14, wherein before carrying out a subsequently defined workflow, the processor unit is adapted to compare the processing steps and the list of mass spectrometry data of the subsequently defined workflow to the processing steps and the list of mass spectrometry data of one or more stored workflows, and if both the processing steps and the list of initial data files of a stored workflow correspond to the initial processing steps of the subsequent workflow, data from the corresponding result file of that stored workflow is retrieved in place of carrying out the initial processing steps of the subsequently defined workflow.

16. The mass-spectrometric molecular compound identification system of claim 10, wherein the storage unit is further adapted to store for each item of processed data which default or dynamic module created or modified this item of processed data.

17. The mass-spectrometric molecular compound identification system of claim 1, further comprising visualization means, wherein the processor unit is further adapted to visualize the grouped, selected and/or modified data of one or more processing steps using the visualization means.

18. The mass-spectrometric molecular compound identification system of claim 1, wherein the instrument interface comprises a bidirectional communication link configured to transmit acquisition-parameter updates from the processor unit to the mass spectrometer during operation.

19. The mass-spectrometric molecular compound identification system of claim 18, wherein the processor unit is adapted to process a first set of mass spectrometry data, performing one or more processing steps, wherein the instrument interface is adapted to send commands to the mass spectrometer, initiating the measurement of a second set of mass spectrometry data, and to receive the second set of mass spectrometry data from the mass spectrometer, wherein the storage unit is adapted to save the second set of mass spectrometry data, and wherein the processor unit is adapted to process the second set of mass spectrometry data, performing one or more processing steps.

20. A mass spectrometry setup comprising a mass-spectrometric molecular compound identification system according to claim 1 and a mass spectrometer.

* * * * *